US010779519B2

(12) United States Patent
Goldman et al.

(10) Patent No.: US 10,779,519 B2
(45) Date of Patent: Sep. 22, 2020

(54) HUMAN GLIAL CHIMERIC MODEL FOR DRUG CANDIDATE ASSESSMENT IN HUMAN GLIOTROPHIC VIRAL INFECTIONS AND PROGRESSIVE MULTIFOCAL ENCEPHALOPATHY

(71) Applicant: University of Rochester, Rochester, NY (US)

(72) Inventors: Steven A. Goldman, Webster, NY (US); Martha Windrem, West Henrietta, NY (US)

(73) Assignee: UNIVERSITY OF ROCHESTER, Rochester, NY (US)

( * ) Notice: Subject to any disclaimer, the term of this patent is extended or adjusted under 35 U.S.C. 154(b) by 0 days.

(21) Appl. No.: 14/710,144

(22) Filed: May 12, 2015

(65) Prior Publication Data

US 2015/0328339 A1 Nov. 19, 2015

Related U.S. Application Data

(60) Provisional application No. 61/992,403, filed on May 13, 2014.

(51) Int. Cl.

| | |
|---|---|
| ***G01N 33/00*** | (2006.01) |
| ***A01K 67/027*** | (2006.01) |
| ***A61K 49/00*** | (2006.01) |
| ***G01N 33/50*** | (2006.01) |
| ***G01N 33/569*** | (2006.01) |
| ***C12Q 1/70*** | (2006.01) |

(52) U.S. Cl.

CPC ...... *A01K 67/0271* (2013.01); *A61K 49/0008* (2013.01); *C12Q 1/701* (2013.01); *G01N 33/5026* (2013.01); *G01N 33/5058* (2013.01); *G01N 33/5088* (2013.01); *G01N 33/56966* (2013.01); *A01K 2207/12* (2013.01); *A01K 2227/105* (2013.01); *A01K 2267/0337* (2013.01); *G01N 2333/025* (2013.01); *G01N 2333/03* (2013.01); *G01N 2333/085* (2013.01); *G01N 2500/10* (2013.01)

(58) Field of Classification Search

CPC ........................ A01K 67/0271; A01K 49/0008

See application file for complete search history.

(56) References Cited

U.S. PATENT DOCUMENTS

| | | | | |
|---|---|---|---|---|
| 5,026,365 | A | 6/1991 | Rossini et al. | |
| 5,082,670 | A | 1/1992 | Gage et al. | |
| 6,245,564 | B1 | 6/2001 | Goldman et al. | |
| 6,497,872 | B1 | 12/2002 | Weiss et al. | |
| 7,524,491 | B2 * | 4/2009 | Goldman ........... | A01K 67/0271 424/93.1 |
| 2003/0223972 | A1 | 12/2003 | Goldman et al. | |
| 2004/0029269 | A1 | 10/2004 | Goldman et al. | |
| 2005/0176626 | A1 | 8/2005 | Goldman et al. | |

FOREIGN PATENT DOCUMENTS

| | | |
|---|---|---|
| WO | 92/04033 | 3/1992 |

OTHER PUBLICATIONS

Maginnis et al (Seminars in Cancer Biology 19 (2009) 261-269).*
Munoz-Sanjuan et al (Expert Opin. Ther. Patents, 19(12): 1639-1646, 2009).*
Haley and Atwood (The Journal of Clinical Investigation, 124(12): 5103-5106, 2014) (Year: 2014).*
Kondo et al., "Human Glial Chimeric Mice Reveal Astrocytic Dependence of JC Virus Infection," J. Clin. Invest. 124 (12):5323-5336 (2014).
Haley et al., "An Animal Model for Progressive Multifocal Leukoencephalopathy," J. Clin. Invest. 124(12):5103-5106 (2014).
Windrem et al., "Fetal and Adult Human Oligodendrocyte Progenitor Cell Isolates Myelinate the Congenitally Dysmyelinated Brain," Nat. Med. 10(1):93-97 (2004).
Abuchowski and Davis, "Soluble Polymer-Enzyme Adducts," In: *Enzymes as Drugs*, Hocenberg and Roberts, eds., Wiley-Interscience (1981).
Aksamit, "Progressive Multifocal Leukoencephalopathy: A Review of the Pathology and Pathogenesis," *Micro. Res. & Techniq.* 32:302-311 (1995).
Araque et al., "Tripartite Synapses: Glia, the Unacknowledged Partner," *Trends Neurosci.* 22:208-215 (1999).
Astrom et al., "Early Pathological Changes in Progressive Multifocal Leukoencephalopathy: A Report of two Asymptomatic Cases Occurring Prior to the AIDS Epidemic," *Acta Neuropathol.* 88:93-105 (1994).
Banin et al., "Enhanced Phosphorylation of p53 by ATM in Response to DNA Damage," *Science* 281:1674-1677 (1998).
Benediktsson et al., "Neuronal Activity Regulates Glutamate Transporter Dynamics in Developing Astrocytes," *Glia* 60:175-188 (2012).
Berger, J.R., "Progressive Multifocal Leukoencephalopathy," *Current Neurology and Neuroscience Reports* 7:461-469 (2007).
Bjorklund and Stenevi (eds), Neural Grafting in the Mammalian CNS, Ch. 3-8, Elsevier, Amsterdam (1985).
Brenner et al., "Apoptosis. Mitochondria-the Death Signal Integrators," *Science* 289:1150-1151 (2000).
Bruck et al., "Reduced Astrocytic NF-kappaB Activation by Laquinimod Protects From Cuprizone-Induced Demyelination," *Acta Neuropathol.* 124:411-424 (2012).

(Continued)

*Primary Examiner* — Anoop K Singh
*Assistant Examiner* — Magdalene K Sgagias
(74) *Attorney, Agent, or Firm* — Troutman Pepper Hamilton Sanders LLP

(57) ABSTRACT

The present invention is directed to a method of assessing in vivo human glial cell response to pathogenic infection that involves providing a non-human mammal either with at least 30% of its glial cells in its corpus callosum being human glial cells and/or with at least 5% of its glial cells its brain and brain stem white matter being human glial cells, subjecting the non-human mammal to pathogenic infection and assessing the in vivo human glial cell response to pathogenic infection. A method of identifying therapeutic agents for the pathogenic infection as well as forms of the non-human mammal having a pathogenic brain infection are also disclosed.

13 Claims, 10 Drawing Sheets

Specification includes a Sequence Listing.

(56) References Cited

OTHER PUBLICATIONS

Busser et al., "Ectopic Cell Cycle Proteins Predict the Sites of Neuronal Cell Death in Alzheimer's Disease Brain," *J. Neurosci.* 18:2801-2807 (1998).
Cambi et al., "Transcriptional Regulation of the rat PLP Promoter in Primary Cultures of Oligodendrocytes," *Neurochem. Res.* 19:1055-60 (1994).
Caracciolo et al., "Role of the Interaction Between Large T Antigen and Rb Family Members in the Oncogenicity of JC Virus," *Oncogene* 25:5294-5301 (2006).
Cook et al., "Regulation of Rodent Myelin Proteolipid Protein Gene Expression," *Neurosci. Lett.* 137(1):56-60 (1992).
DeCaprio et al., "SV40 Large Tumor Antigen Forms a Specific Complex with the Product of the Retinoblastoma Susceptibility Gene," *Cell* 54:275-283 (1988).
Demeter, "JC, BK, and Other Polyomaviruses; Progressive Multifocal Leukoencephalopathy," *Mandell, Douglas and Bennett's Principles and Practice of Infectious Diseases*, vol. 2, 4th Ed., New York, NY: Churchill Livingstone, pp. 1400-1406 (1995).
Desagher et al., "Mitochondria as the Central Control Point of Apoptosis," *Trends Cell Biol.* 10:369-377 (2000).
Dickmanns et al., "The Kinetics of Simian Virus 40-Induced Progression of Quiescent Cells into S Phase Depend on Four Independent Functions of Large T Antigen," *J. Virol.* 68:5496-5508 (1994).
Finkel, "The Mitochondrion: is it Central to Apoptosis?" *Science* 292:624-626 (2001).
Frisque, "Regulatory Sequences and Virus-cell Interactions of JC Virus," *Prog. Clin. Biol. Res.* 105:41-59 (1983).
Funfschilling et al., "Glycolytic Oligodendrocytes Maintain Myelin and Long-term Axonal Integrity," *Nature* 485:517-521 (2012).
Gerber et al., "Immunohistochemical Demonstration of Common Antigen of Polyomaviruses in Routine Histologic Tissue Sections of Animals and Man," *Am. J. Clin. Pathol.* 73:795-797 (1980).
Gloster et al., "The T alpha 1 alpha-tubulin Promoter Specifies Gene Expression as a Function of Neuronal Growth and Regeneration in Transgenic Mice ," *J. Neurosci.* 14:7319-30 (1994).
Gorelik et al., "Progressive Multifocal Leukoencephalopathy (PML) Development is Associated With Mutations in JC Virus Capsid Protein VP1 That Change its Receptor Specificity," *J. Infect. Dis.* 204:103-114 (2011).
Greenlee et al., "Immunoenzymatic Labelling of JC Papovavirus T Antigen in Brains of Patients with Progressive Multifocal Leukoencephalopathy," *Acta Neuropathol.* 71:150-153 (1986).
Gruber, "The case for local immunosuppression," *Transplantation* 54:1-11 (1992).
Han et al., "Forebrain Engraftment by Human Glial Progenitor Cells Enhances Synaptic Plasticity and Learning in Adult Mice," *Cell Stem Cell* 12:342-353 (2013).
Hermeking et al., "Role of C-myc in Simian Virus 40 Large Tumor Antigen-Induced DNA Synthesis in Quiescent 3T3-L1 Mouse Fibroblasts," *Proc. Nat'l. Acad. Sci. USA* 91:10412-10416 (1994).
Herrup et al., "Divide and Die: Cell Cycle Events as Triggers of Nerve Cell Death," *J. Neurosci.* 24:9232-9239 (2004).
Holmseth et al., "Specificity Controls for Immunocytochemistry: The Antigen Preadsorption Test Can Lead to Inaccurate Assessment of Antibody Specificity," *The J. Histochem. and Cytochem.* 60:174-187 (2012).
Holst et al., "Binding and Activation of the Promoter for the Neural Cell Adhesion Molecule by Pax-8," *J. Biol. Chem.* 269:22245-52 (1994).
Ikegaya et al, "Detection of Identical JC virus DNA Sequences in Both Human Kidneys," *Arch. of Virol.* 149:1215-1220 (2004).
Ironside et al., "The Identification of Cells Containing JC Papovavirus DNA in Progressive Multifocal Leukoencephalopathy by Combined in Situ Hybridization and Immunocytochemistry," *J. Pathol.* 157:291-297 (1989).
Jochum et al., "Detection of JC Virus by Anti-VP1 Immunohistochemistry in Brains With Progressive Multifocal Leukoencephalopathy," *Acta Neuropathol.* 94:226-231 (1997).
Kang et al., "Astrocyte-Mediated Potentiation of Inhibitory Synaptic Transmission," *Nature Neurosci.* 1:683-692 (1998).
Keyoung et al., "High-Yield Selection and Extraction of two Promoter-Defined Phenotypes of Neural Stem Cells From the Fetal Human Brain," *Nature Biotech.* 19:843-850 (2001).
Kim et al., "Glial Cell-Specific Regulation of the JC Virus Early Promoter by Large T Antigen," *J. Virol.* 74:755-763 (2000).
Krebs et al., "The JC Virus Minimal Core Promoter is Glial Cell Specific in Vivo," *J. Virol.* 69:2434-42 (1995).
Krynska et al., "Role of Cell Cycle Regulators in Tumor Formation in Transgenic Mice Expressing the Human Neurotropic Virus, JCV, Early Protein," *J. Cell Biochem.* 67:223-230 (1997).
Laszkiewicz et al., "Structural Characterization of Myelin-Associated Glycoprotein Gene Core Promoter," *J. Neurosci. Res.* 50(6):928-36 (1997).
Lincz LF, "Deciphering the Apoptotic Pathway: All Roads Lead to Death," Immunol. *Cell Biol.* 76:1-19 (1998).
Liu et al., "CD44 Expression Identifies Astrocyte-Restricted Precursor Cells," *Dev. Biol.* 276:31-46 (2004).
Liu et al., "Isolation and Sequencing of the 5' end of the rat Microtubule-Associated Protein (MAP1B)-Encoding cDNA," *Gene* 171:307-08 (1996).
London et al., "Brain Tumors in Owl Monkeys Inoculated with a Human Polyomavirus (JC Virus)," *Science* 201:1246-1249 (1978).
Major et al., "Human Fetal Astrocytes in Culture Support the Growth of the Neurotropic Human Polyomavirus, JCV," *J Neuropathol. Exp. Neurol.* 48:425-436 (1989).
Major, E.O., "Progressive Multifocal Leukoencephalopathy in Patients on Immunomodulatory Therapies," *Annu. Rev. Med.* 61:35-47 (2010).
Manfredi et al., "The Transforming Activity of Simian Virus 40 Large Tumor Antigen," *Biochim. Biophys. Acta* 1198:65-83 (1994).
Mazlo et al., "Morphological Demonstration of the First Phase of Polyomavirus Replication in Oligodendroglia Cells of Human Brain in Progressive Multifocal Leukoencephalopathy (PML)," *Acta Neuropathol.* 49:133-143 (1980).
Messam et al., "Lineage Pathway of Human Brain Progenitor Cells Identified by JC Virus Susceptibility," *Ann. Neurol.* 53:636-646 (2003).
Mombaerts et al., "RAG-1-Deficient Mice Have no Mature B and T lymphocytes," *Cell* 68:869-877 (1992).
Monaco et al., "Progenitor-Derived Oligodendrocyte Culture System From Human Fetal Brain," *J. Vis. Exp.* 70:e4274 (2012).
Negoescu et al., "In Situ Apoptotic Cell Labeling by the TUNEL Method: Improvement and Evaluation on Cell Preparations," *J. Histochem. Cytochem.* 44:959-968 (1996).
Nunes et al., "Identification and Isolation of Multipotential Neural Progenitor Cells from the Adult Human White Matter," *Nature Publishing Group* (2003).
Orba et al., "Large T Antigen Promotes JC Virus Replication in G2-Arrested Cells by Inducing ATM-and ATR-Mediated G2 Checkpoint Signaling," *J. Biol. Chem.* 285:1544-1554 (2010).
Padgett et al, "Cultivation of Papova-Like Virus From Human Brain With Progressive Multifocal Leukoencephalopathy," *Lance.* 1257-1260 (1971).
Park et al., "Analysis of Upstream Elements in the HuC Promoter Leads to the Establishment of Transgenic Zebrafish with Fluorescent Neurons," *Dev. Biol.* 227(2):279-93 (2000).
Paukert et al., "Reduction of Motion Artifacts During in Vivo two-Photon Imaging of Brain Through Heartbeat Triggered Scanning," *J. Physiol.* 590:2955-2963 (2012).
Pfister et al., "JC Virus Regulatory Region Tandem Repeats in Plasma and Central Nervous System Isolates Correlate With Poor Clinical Outcome in Patients With Progressive Multifocal Leukoencephalopathy," *J. Virol.* 75:5672-5676 (2001).
Pina-Oviedo et al., "Effects of JC Virus Infection on Anti-apoptotic Protein Surviving in Progressive Multifocal Leukoencephalopathy," *Am. J. Pathol.* 170:1291-1304 (2007).
Radhakrishnan et al., "JC Virus-Induced Changes in Cellular Gene Expression in Primary Human Astrocytes," *J. Virol.* 77:10638-10644 (2003).
Reid et al., "Sequencing and Analysis of JC Virus DNA From Natalizumab-Treated PML Patients," *J. Infect. Dis.* 204:237-244 (2011).

(56) References Cited

OTHER PUBLICATIONS

Richardson-Burns et al., "Progressive Multifocal Leukoencephalopathy and Apoptosis of Infected Oligodendrocytes in the Central Nervous System of Patients With and Without AIDS," *Arch. Neurol.* 59:1930-1936 (2002).
Roy et al., Lazzarini, *Myelin Biology and Disorders* 2nd Ed., San Diego, California: Elsevier Academic Press, pp. 259-287 (2004).
Saenz-Robles et al., "Intestinal Hyperplasia Induced by Simian Virus 40 Large Tumor Antigen Requires E2F2," *J. Virol.* 81:13191-13199 (2007).
Scherer et al., "Differential Regulation of the 2',3'-cyclic nucleotide 3'-Phosphodiesterase Gene During Oligodendrocyte Development," *Neuron* 12:1363-75 (1994).
Seth et al., "JC Virus Induces Nonapoptotic Cell Death of Human Central Nervous System Progenitor Cell-Derived Astrocytes," *J. Virol.* 78:4884-4891 (2004).
Shieh et al., "DNA Damage-Induced Phosphorylation of p53 Alleviates Inhibition by MDM2," *Cell* 91:325-334 (1997).
Shinkai et al., "RAG-2-Deficient Mice Lack Mature Lymphocytes Owing to Inability to Initiate V(D)J Rearrangement ," *Cell* 68:855-867 (1992).
Schultz et al., "NOD/LtSz-Rag1nullPfpnull Mice: a New Model System With Increased Levels Of Human Peripheral Leukocyte and Hematopoietic Stem-Cell Engraftment," *Transplantation* 76:1036-42 (2003).
Sim et al., "CD140a Identifies a Population of Highly Myelinogenic, Migration-Competent and Efficiently Engrafting Human Oligodendrocyte Progenitor Cells," *Nature Biotechnol.* 29:934-941 (2011).
Slee et al., "Serial killers: Ordering Caspase Activation Events in Apoptosis," *Cell Death Differ.*, 6:1067-74 (1999).
Smithies et al., "Insertion of DNA Sequences Into the Human Chromosomal Beta-Globin Locus by Homologous Recombination," *Nature* 317:230-234 (1985).
Springer et al., "A Rapid and Sensitive Assay for Measuring Mitochondrial Metabolic Activity in Isolated Neural Tissue," *Brain Res. Protoc.* 2(4):259-263 (1998).
Sunyaev et al., "Adaptive Mutations in the JC Virus Protein Capsid Are Associated With Progressive Multifocal Leukoencephalopathy (PML)," *PloS Genet.* 5:01000368 (2009).
Tevethia et al., "A Simian Virus 40 Large T-Antigen Segment Containing Amino Acids 1 to 127 and Expressed Under the Control of the rat Elastase-1 Promoter Produces Pancreatic Acinar Carcinomas in Transgenic Mice," *J. Virol.* 71:8157-8166 (1997).
Van Engeland et al., "Annexin V-affinity Assay: a Review on an Apoptosis Detection System Based on Phosphatidylserine Exposure," *Cytometry* 31:1-9 (1998).
Walker et al., "Human Papovavirus (JC): Induction of Brain Tumors in Hamsters," *Science* 181:674-676 (1973).
Wight et al., "Regulation of Murine Myelin Proteolipid Protein Gene Expression," *J. Neurosci. Res.* 50(6):917-27 (1997).
Will et al., "Analysis of Mitochondrial Function Using Phosphorescent Oxygen-Sensitive Probe," *Nat. Protoc.* 1:2563-72 (2006).
Windrem et al., "Fetal and Adult Human Oligodendrocyte Progenitor Cell Isolates Myelinate the Congenitally Dysmyelinated Brain," *Nature Med.* 10:93-97 (2004).
Windrem et al., "Neonatal Chimerization With Human Glial Progenitor Cells Can Both Remyelinate and Rescue the Otherwise Lethally Hypomyelinated Shiverer Mouse," *Cell Stem Cell* 2:553-565 (2008).
Wrabetz et al., "Analysis of the Human MBP Promoter in Primary Cultures of Oligodendrocytes: Positive and Negative cis-Acting Elements in the Proximal MBP Promoter Mediate Oligodendrocyte-Specific Expression of MBP," *J. Neurosci. Res.* 36:455-71 (1993).
Xiao et al., "Astrocyte Inactivation of the pRb Pathway Predisposes Mice to Malignant Astrocytoma Development that is Accelerated by PTEN Mutation," *Cancer Cell* 1:157-168 (2002).
Yang et al., "Neuronal Cell Death is Preceded by Cell Cycle Events at all Stages of Alzheimer's Disease," *J. Neurosci.* 23:2557-2563 (2003).
Yao et al., "Neural Specificity of ELAV Expression: Defining a *Drosophila* Promoter for Directing Expression to the Nervous System," *J. Neurochem.* 63(1):41-51 (1994).
Zurhein et al., "Particles Resembling Papova Viruses in Human Cerebral Demyelinating Disease," *Science* 148:1477-1479 (1965).

* cited by examiner

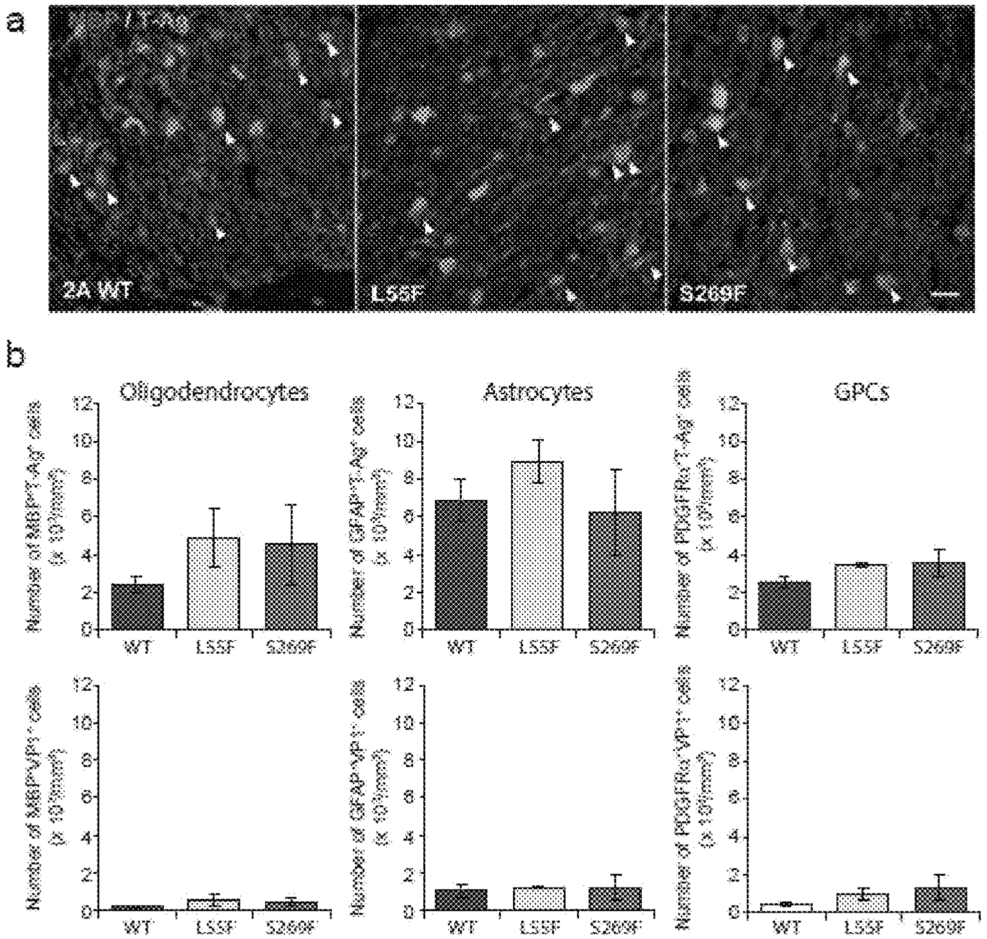
Figures 10A-B

HUMAN GLIAL CHIMERIC MODEL FOR DRUG CANDIDATE ASSESSMENT IN HUMAN GLIOTROPHIC VIRAL INFECTIONS AND PROGRESSIVE MULTIFOCAL ENCEPHALOPATHY

This application claims the benefit of U.S. Provisional Patent Application Ser. No. 61/992,403, filed May 13, 2014, which is hereby incorporated by reference in its entirety

FIELD OF THE INVENTION

The present application relates to a human glial chimeric model for drug candidate assessment in human gliotrophic viral infections and progressive multifocal encephalopathy.

BACKGROUND OF THE INVENTION

Progressive multifocal leukoencephalopathy (PML) is a demyelinating condition characterized by the degenerative loss of cerebral white matter following infection by JC virus (JCV), a normally latent polyoma virus that becomes virulent in the setting of immunosuppression (Berger, J. R., "Progressive Multifocal Leukoencephalopathy," *Current Neurology and Neuroscience Reports* 7:461-469 (2007); Major, E. O., "Progressive Multifocal Leukoencephalopathy in Patients on Immunomodulatory Therapies," *Annu Rev Med* 61:35-47 (2010)). PML is an extremely debilitating demyelination disease of the central nervous system. PML is generally characterized by neurological deficits that progress rapidly, typically without signs of intracranial pressure, including hemiparesis, cognitive disturbance, visual field deficits, ataxia, aphasia, cranial nerve deficits and sensory deficits. Patients who have PML typically deteriorate rapidly and death commonly occurs within 6 months of diagnosis (Demeter L M., "JC, BK, and Other Polyomaviruses; Progressive Multifocal Leukoencephalopathy," In Mandell G L, Bennett J E, Dolin, eds. *Mandell, Douglas and Bennett's Principles and Practice of Infectious Diseases,* 4th edition. Vol. 2. New York, N.Y.: Churchill Livingstone; 1995: 1400-1406). Subjects most susceptible to PML are subjects that are immuno-compromised (e.g., AIDS patients) or subjects undergoing treatment with immunosuppressants (for instance after organ transplant or to treat an inflammation related condition such as multiple sclerosis or rheumatoid arthritis).

Primary infection with JCV can occur asymptomatically during childhood (Padgett et al, *Lancet.,* 1257-1260 (1971). JCV is then disseminated throughout the body, probably through viraemia (Ikegaya et al, *Arch. of Virol.* 149: 1215-1220 (2004)). It is thought that JCV persists mostly in brain and renal tissue. JCV is gliotropic and associated with oligodendrocytic loss in humans, but the human-selective nature of its infectivity and glial pathology has prevented the establishment of informative animal models.

The present invention is directed to overcoming these and other deficiencies in the art.

SUMMARY OF THE INVENTION

One aspect of the present invention is directed to a method of assessing in vivo human glial cell response to pathogenic infection. This method involves providing a non-human mammal either with at least 30% of its glial cells in its corpus callosum being human glial cells and/or with at least 5% of its glial cells in its brain and brain stem white matter being human glial cells, subjecting the non-human mammal to pathogenic infection, and assessing, as a result of the subjecting step, the in vivo human glial cell response to pathogenic infection.

Another embodiment of the present invention relates to a method of identifying an agent suitable for treating or inhibiting a pathogenic brain infection. This method involves providing a non-human mammal with at least 30% of its glial cells in its corpus callosum being human glial cells and/or with at least 5% of its glial cells in its brain and brain stem white matter being human glial cells and providing a candidate agent. The non-human mammal is exposed to an infective brain pathogen under conditions effective to establish a brain infection and the candidate agent is administered to the non-human mammal prior to, concurrent with, or after exposing. As a result of administering, one or more indices of pathogenic brain infection are assessed to identify an agent suitable for treating or inhibiting the pathogenic brain infection.

A further aspect of the present invention pertains to a non-human mammal with at least 30% of all of its glial cells in its corpus callosum being human glial cells and/or at least 5% of all of its glial cells in the white matter of its brain and/or brain stem being human glial cells, where the non-human mammal has a pathogenic brain infection.

In the work corresponding to the present invention, newborn immunodeficient homozygous shiverer (rag2−/−xshi/shi) mice were engrafted with bipotential glial progenitor cells (GPCs) isolated from fetal human brain tissue, thereby generating human glial-chimeric mouse brains, in which most murine glia are ultimately replaced by human oligodendrocytes, astrocytes and their progenitors. Once these animals had grown to maturity, they were injected intracerebrally with live JCV of several distinct virulent strains, including types 1a (Mad-1) and 2a, and several patient-isolated mutant isoforms thereof (Sunyaev et al., "Adaptive Mutations in the JC Virus Protein Capsid Are Associated with Progressive Multifocal Leukoencephalopathy (PML)," *PloS Genetics* 5:e1000368 (2009), which is hereby incorporated by reference in its entirety), and the consequent JCV infection of GPCs, astrocytes and oligodendrocytes was assessed using immunolabeling for both the early viral large T antigen and the VP-1 capsid protein. It was found that the JCV-injected human glial chimeric mice developed widespread infection of their integrated human glia, and that this process was accompanied by local demyelination in association with regions of frank gliosis. Cultures of human fetal glial progenitor cells and their progeny were also infected with JCV, to assess the cellular mechanisms of JCV toxicity as concurrent functions of time, cell cyclicity and phenotype. In brief, it was found that the principal targets of JCV are GPCs and astrocytes, that oligodendroglia are also infected but later and less efficiently, that the virus actively mutates with viral spread, and most remarkably, that infected oligodendroglia are not even necessary for viral propagation and spread. This data thus indicate that JCV is principally a disease of astrocytes and their progenitors, with oligodendrocytic loss and demyelination a pathogenic but unnecessary concomitant to viral infection and spread.

BRIEF DESCRIPTION OF THE DRAWINGS

FIG. 1A shows both T-Ag (left panels) and VP1 (right panels) were expressed by CD140a+ GPCs grown in suspension culture. Both viral antigens were more abundantly expressed at 10 days post-infection (DPI) than at 3 DPI. As shown in FIG. 1B, in CD44+ MACS-derived astrocytes, T antigen was expressed as early as 1 DPI, whereas VP1 was first expressed at 3 DPI. As shown in FIG. 1C, in contrast, oligodendrocytic infection in vitro was both delayed and of relatively low efficiency, showing weak T antigen expression without VP1 at 5 DPI (arrowheads), and only scattered VP1+ oligodendroglia at 10 DPI. These infected oligodendrocytes appeared to exhibit rapid cytolytic death. Together, these events resulted in the progressive accumulation of infected astroglia following initial infection. In FIG. 1D, representative images of a JCV infected T-antigen+/VP1+ oligodendrocyte at 10 DPI showing nuclear hypertrophy is apparent. As shown in FIG. 1E, when assessed at 5 DPI, T antigen-defined oligodendroglial infection was of significantly lower efficiency than that of astrocytes, while VP1-defined JCV replication was markedly less frequent in oligodendrocytes. Data presented as percentage of cells of each phenotype at 5 DPI. Scale: 20 μm.

FIG. 2A shows confocal images of infected oligodendrocytes, astrocytes, and GPCs in shiverer mice neonatally engrafted with human GPCs and infected with Type 1A (Mad-1) JCV for 12 weeks. As shown in FIG. 2B, by 12 weeks, infected astrocytes were highly abundant and largely magnocellular, with overtly enlarged nuclei and bizarrely fibrotic processes. As shown in FIG. 2C, in contrast, substantial human oligodendrocytic loss was evident by 12 weeks after infection, and most of the infected remainder expressed LgT, as exemplified by these LgT+/MBP+ oligodendroglia. Only human oligodendroglia express MBP in the shiverer brain. FIG. 2D shows that infection was restricted to human cells. In this example, unengrafted mouse corpus callosum manifested no evidence of infection 12 weeks after JCV injection. Scale: a, 20 μm; b-c, 50 μm; d, 100 μm.

In FIGS. 3A-B, at 4 weeks after viral infection, focal regions of demyelination (FIG. 3A, arrows) and infection associated astrogliosis (FIG. 3B, arrow) were noted in the forebrain white matter of infected mice, typically in discrete foci abutting the callosal wall of the lateral ventricle. As shown in FIGS. 3C-D, by 11 weeks after infection, diffuse hypomyelination of the callosa and capsules of infected chimeric mice was noted. FIG. 3E shows that uninfected human chimeric controls by 20 weeks after transplantation exhibited dense GPC-derived myelination, as did JCV-injected non-xenografted murine controls. Scale: A, C, 200 μm; B, D, E, 100 μm.

As shown in FIG. 4A, JCV spread preferentially in the white matter in the chimerized shiverer mice, in which a large proportion of human cells are oligodendrocytes. VP1+ human cells became progressively more widespread with time, with infection progressing from the site of viral injection to include much of the central white matter by 12 weeks post-infection. As shown in FIG. 4B, both LgT and VP1-expressing cells, which respectively comprise all JCV and those in which viral replication has occurred, accumulated as a function of time. When analyzed by phenotype (see FIGS. 4C-E), the absolute number and relative proportion of LgT+ oligodendrocytes (FIG. 4C) was lower than that of astrocytes (FIG. 4D) and GPCs (FIG. 4E), at all time-points examined.

FIG. 5A shows that JCV introduced into myelin wild-type mice, which are colonized with human progenitors and astrocytes, but not oligodendrocytes, yielded viral propagation and geographic spread that was as rapid and extensive as that noted in human glial chimeric shiverer mice, in which human oligodendroglia are densely represented. These schematics show the distributions of large T antigen+(left) and VP-1+(right) cells mapped in 14 μm sagittal sections of myelin wild-type, rag1−/− mice injected with JCV as adults, 12 weeks previously. Infected human cells are widely distributed, despite the absence of human oligodendroglia in these brains. FIG. 5B shows a sagittal section along the callosal length of a myelin wild-type, glial chimeric mouse 12 weeks post-infection, showing widespread infection and VP-1 expression by both GFAP+ subcortical human astrocytes and GFAP− cortical human astrocytes and glial progenitors. As set forth in FIG. 5C, higher magnification views show the predominance of infected cells in the cortical grey, which include both LgT+(FIG. 5D) and VP1+(FIG. 5E) glia, manifesting the typical hypertrophic nuclei of cells that have undergone viral replication. By way of comparison, the image of FIG. 5F shows VP1+ glia in the corpus callosum of a human glial chimeric shiverer mouse 12 wks after type 1A (Mad-1) JCV infection, showing the predominant white matter spread of virus in these mice, which manifest both oligodendrocytic and astrocytic infection (compare to FIG. 5C). Scale: FIGS. 5A-B, 100 μm; FIGS. 5C-E, 50 μm.

In FIGS. 6A-B, Mad-1 JCV-infected MBP+ oligodendrocytes were frequently noted to co-express Ki67, a marker of mitotic entry, suggesting the aberrant entry of these typically post-mitotic cells into cell cycle. FIG. 6A shows a representative Ki67+, LgT+/MBP+ oligodendrocyte in the corpus callosum of a human glial chimeric shiverer mouse, 12 weeks post-infection. FIG. 6B shows that whereas roughly a third of all infected oligodendroglia expressed Ki67 at this time-point, no Ki767+ oligodendrocytes were noted in uninfected controls. As shown in FIG. 6C, LgT+Ki67+ oligodendrocytes were common in vitro, and most LgT+ oligodendroglia expressed Ki67, while few if any uninfected oligodendroglia expressed Ki67 (FIG. 6D). In culture, JCV infection significantly reduced the number of oligodendrocytes at 10 DPI (FIG. 6E) by inducing TUNEL-defined apoptosis (FIG. 6F). At 10 DPI, among the infected TUNEL+ oligodendrocytes, 43.5±2.1% were LgT+, while only 4.6±0.3% were VP1+ (FIG. 6G), indicating the failure of most infected oligodendroglia to progress to VP1-defined viral replication before dying. As shown in FIG. 6H, TUNEL expression by T-Ag+ pyknotic O4+ oligodendrocytes was typical, although less common VP1+O4-defined oligodendroglia were noted (FIG. 6I), which typically were TUNEL- and had hypertrophic nuclei, reflecting the quantitation of (FIG. 6G). p<0.01, *p<0.001, by paired t-test; b, n=3 animals each group; d-e, n=4 runs, triplicate wells. Scale: FIG. 6A, 10 μm; FIG. 6C, 20 μm.

FIG. 7A shows LgT antigen+GFAP-defined astrocytes co-expressed phospho-p53(Ser15), associated with G2M arrest. FIG. 7B shows that neither vehicle-treated nor LgT-astroglia in infected cultures did so to any significant degree. FIGS. 7C-D show JCV-infected, LgT antigen+ post-mitotic oligodendrocytes expressed phospho-p53(Ser15) as well, as did CD140a+ GPCs (FIGS. 7E-F); in both phenotypes, LgT antigen+ cells were significantly more likely to express phosphor-p53 (Ser15). FIGS. 7G-H show vehicle-treated and uninfected GPCs expressed intranuclear cyclin B1 only when mitotic and in M phase (the latter as assessed by DAPI staining) (upper panel, arrows), whereas the nuclei of JCV-infected GPCs admitted cyclin B1 in a temporally promiscuous fashion (lower panel, arrowheads). As shown in FIG. 7I, nuclear phospho-p53 and cyclin B1 were co-expressed by mitotically-arrested infected astrocytes, but not by uninfected astrocytes. FIG. 7J shows that like control GPCs, uninfected astrocytes expressed intranuclear cyclin B1 only in M phase, while JCV-infected astrocytes expressed nuclear cyclin B1 even when not dividing. All cultures assessed at 10 DPI with type 2A (Mad-1 NCCR) JCV. Scale=20 μm.

FIG. 8A shows that infected astrocytes exhibit G2 accumulation. Cell cycle analysis was performed on JCV-infected human astroglia, derived from GPCs exposed to high serum for 10 days, then exposed to JCV and analyzed 14 days later. The relative percentages of cells in each stage of the cell cycle were compared between vehicle-treated and JCV-infected astrocytes, using the Dean-Jett-Fox model in FlowJo. This analysis revealed that JCV-infected, T antigen$^+$ astrocytes exhibited a marked accumulation of cells in G2 relative to uninfected controls. FIG. 8B shows that infected oligodendrocytes, like astroglia, manifest nuclear hypertrophy. Morphometry revealed that VP1-expressing oligodendrocytic nuclei were typically enlarged relative to those of uninfected cells (graph, right), and had significantly higher DNA content (graph, left). Photomicrographs of O4$^+$ oligodendrocytes were recorded with a constant exposure time for the DAPI signal. The areas and total fluorescence intensities of individual DAPI$^+$ nuclei were analyzed using ImageJ (Ver. 1.45s, NIH). Data are represented as means±SEM from 3 experiments. Numbers in bars indicate the numbers of analyzed nuclei. One-way ANOVA followed by Bonferroni post-hoc test. p*<0.05, p<0.01, p*<0.001.

FIGS. 10A-B show in vivo infection by JCV mutants. JCV VP1 mutants manifested no phenotypic preferences in vivo. Type 2A (Mad-1 NCCR) JCV with WT or mutant VP1 was injected into the corpus callosum of human glial chimeric shiverer×rag2-null mice at 17 weeks of age, and the mice killed 5 weeks later. As shown in FIG. 10A, MBP$^+$ mature oligodendrocytes in the corpus callosum were infected by WT virus and both the L55F and S269F muteins equally. FIG. 10B shows quantification of T-Ag$^+$ and VP1$^+$ infected cells in the corpus callosum. Using one-way ANOVA, no statistically significant differences were noted in the infectivity of these viral genotypes (p>0.05 for all comparisons). Means±SEM, corrected for the number of human nuclear antigen$^+$ cells (n=3-5).

DETAILED DESCRIPTION OF THE INVENTION

Figure 1:
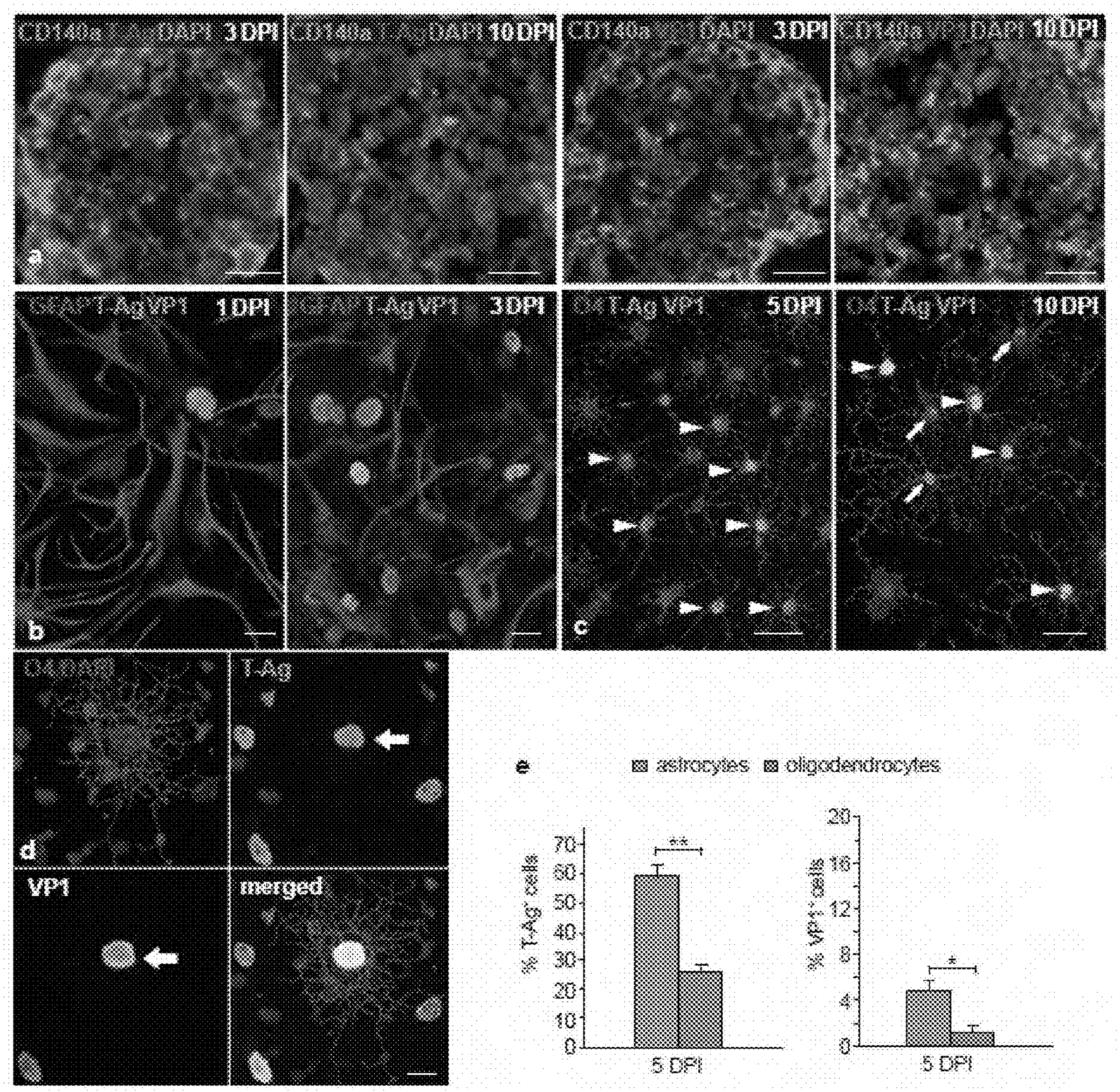
FIGS. 1A-E show human astroglia are most efficiently infected by JCV in vitro. Human glial progenitor cells (GPCs) and astrocytes were readily infected by JCV in vitro, with robust expression within days of both the early viral large T antigen and the later VP1 capsid protein.

One aspect of the present invention is directed to a method of assessing in vivo human glial cell response to pathogenic infection. This method involves providing a non-human mammal either with at least 30% of its glial cells in its corpus callosum being human glial cells and/or with at least 5% of its glial cells in its brain and brain stem white matter being human glial cells, subjecting the non-human mammal to pathogenic infection, and assessing, as a result of the subjecting step, the in vivo human glial cell response to pathogenic infection.

Preferably, at least 50% (more preferably, at least 70%, and most preferably at least 90%) of all glial cells in the corpus callosum of the non-human mammal are human glial cells. Alternatively, at least 10% (preferably), at least 15% (more preferably), or at least 20% (most preferably) of all glial cells in the white matter of the non-human mammal's brain and/or brain stem are human glial cells. In another embodiment, the white matter is cerebellar white matter and at least 50% of all glial cells in the cerebellar white matter are human glial cells.

The pathogen may be a glial cell-specific pathogen or a human-specific pathogen. Preferably, the pathogen is a virus. More preferably, the virus is JC virus, herpes virus-1, herpes virus-2, herpes virus-6, herpes virus-8, cytomegalovirus, Epstein-Barr virus, Cocksackie virus, or varicella.

Methods of making the non-human mammal are described in U.S. Pat. No. 7,524,491 to Goldman and Windrem et al., "Neonatal Chimerization With Human Glial Progenitor Cells Can Both Remyelinate and Rescue the Otherwise Lethally Hypomyelinated Shiverer Mouse," *Cell Stem Cell* 2:553-565 (2008), which are hereby incorporated by reference in their entirety.

The non-human mammal can be any pre-natal, neo-natal, or adult non-human mammal. Any non-human mammal is suitable for carrying out the present invention, including mice, rats, guinea pigs and other small rodents, dogs, cats, sheep, goats, and monkeys. In a preferred embodiment of the present invention, the non-human mammal is a mouse.

It is desirable that the non-human mammal host accepts the human glial cells with little or no adverse immune recognition. Therefore, it is preferred that the non-human mammal is immuno-incompetent, immuno-deficient, or immuno-suppressed.

Immunosuppression can be achieved either through the administration of immunosuppressive drugs such as cyclosporin, sirolimus, or tacrolimus, or through strategies employing locally applied immunosuppressants. Local immunosuppression is disclosed by Gruber, *Transplantation* 54:1-11 (1992), which is hereby incorporated by reference in its entirety. U.S. Pat. No. 5,026,365 to Rossini, which is hereby incorporated by reference in its entirety, discloses encapsulation methods also suitable for local immunosuppression.

As an alternative to employing immunosuppression techniques, methods of gene replacement or knockout using homologous recombination, as taught by Smithies et al. *Nature* 317:230-234 (1985), which is hereby incorporated by reference in its entirety, can be applied to donor glial cells for the ablation of major histocompatibility complex (MHC)

genes. Donor glial cells lacking MHC expression would allow for the transplantation of an enriched glial cell population across allogeneic and perhaps even xenogenic, histocompatibility barriers without the need to immunosuppress the recipient. General reviews and citations for the use of recombinant methods to reduce antigenicity of donor cells are also disclosed by Gruber, *Transplantation* 54:1-11 (1992), which is hereby incorporated by reference in its entirety. Exemplary approaches to reduce immunogenicity of transplants by surface modification are disclosed in WO92/04033 to Faustman, which is hereby incorporated by reference in its entirety.

Alternatively, the immunogenicity of the transplanted cells may be reduced by using any non-human mammal host that possesses a genetic mutation rendering it immunodeficient. Exemplary animal models include those having a mutation which disrupts the recombination activating gene 2 (Rag2) (Shinkai et al., *Cell* 68:855-867 (1992), which is hereby incorporated by reference in its entirety) or the Rag1 gene (Mombaerts et al., *Cell* 68:869-877 (1992) and Schultz et al., *Transplantation* 76:1036-42 (2003), which are hereby incorporated by reference in their entirety). Other immunodeficient animal models useful for practicing the present invention include any of the severe combined immunodeficient mice (SCID), having a mutation in the Prkdc gene. Preferred SCID mouse models for use in the present invention include the NOD-SCID, the NOD-SCID-IL2rg, and the NOG (NOD-SCID/$\gamma c^{null}$) mouse models. Additionally, the Nude mouse models, carrying a mutation in the Foxn1 gene are also useful for practicing the present invention.

In accordance with the present invention, the population of human glial cells to be transplanted into the non-human mammal host animal are preferably bipotential glial progenitor cells. In one embodiment, the glial progenitor cells can be biased to producing oligodendrocytes. Alternatively, the glial progenitor cells can be biased to producing astrocytes. In a further embodiment, the human glial cells to be transplanted into the non-human mammal host animal can be astrocytes.

Glial progenitor cells can be obtained from embryonic, fetal, or adult brain tissue, embryonic stem cells, or induced pluripotential cells. Preferably, the glial progenitor cells are isolated from ventricular and subventricular zones of the brain or from the subcortical white matter.

Glial progenitor cells can be extracted from brain tissue containing a mixed population of cells directly by using the promoter specific separation technique, as described in U.S. Patent Application Publication Nos. 20040029269 and 20030223972 to Goldman, which are hereby incorporated by reference in their entirety. This method involves selecting a promoter which functions specifically in glial progenitor cells, and introducing a nucleic acid encoding a marker protein under the control of said promoter into the mixed population cells. The mixed population of cells is allowed to express the marker protein and the cells expressing the marker protein are separated from the population of cells, with the separated cells being the glial progenitor cells.

Glial specific promoters that can be used for isolating glial progenitor cells from a mixed population of cells include the CNP promoter (Scherer et al., *Neuron* 12:1363-75 (1994), which is hereby incorporated by reference in its entirety), an NCAM promoter (Holst et al., *J. Biol. Chem.* 269:22245-52 (1994), which is hereby incorporated by reference in its entirety), a myelin basic protein promoter (Wrabetz et al., *J. Neurosci. Res.* 36:455-71 (1993), which is hereby incorporated by reference in its entirety), a JC virus minimal core promoter (Krebs et al., *J. Virol.* 69:2434-42 (1995), which is hereby incorporated by reference in its entirety), a myelin-associated glycoprotein promoter (Laszkiewicz et al., "Structural Characterization of Myelin-associated Glycoprotein Gene Core Promoter," *J. Neurosci. Res.* 50(6): 928-36 (1997), which is hereby incorporated by reference in its entirety), or a proteolipid protein promoter (Cook et al., "Regulation of Rodent Myelin Proteolipid Protein Gene Expression," *Neurosci. Lett.* 137(1): 56-60 (1992); Wight et al., "Regulation of Murine Myelin Proteolipid Protein Gene Expression," *J. Neurosci. Res.* 50(6): 917-27 (1997); and Cambi et al., *Neurochem. Res.* 19:1055-60 (1994), which are hereby incorporated by reference in their entirety). See also U.S. Pat. No. 6,245,564 to Goldman et. al., which is hereby incorporated by reference in its entirety.

Alternatively, it may be preferable to isolate the glial progenitor cells by first removing neurons or neural progenitor cells from the mixed cell population. Where neuronal progenitor cells are to be separated from the mixed population of cells, they can be removed based on their surface expression of NCAM, PSA-NCAM, or any other surface moiety specific to neurons or neural progenitor cells. Neurons or neural progenitor cells may also be separated from a mixed population of cells using the promoter based separation technique. Neuron or neural progenitor specific promoters that can be used for separating neural cells from a mixed population of cells include the Tα1 tubulin promoter (Gloster et al., *J. Neurosci.* 14:7319-30 (1994), which is hereby incorporated by reference in its entirety), a Hu promoter (Park et al., "Analysis of Upstream Elements in the HuC Promoter Leads to the Establishment of Transgenic Zebrafish with Fluorescent Neurons," *Dev. Biol.* 227(2): 279-93 (2000), which is hereby incorporated by reference in its entirety), an ELAV promoter (Yao et al., "Neural Specificity of ELAV Expression: Defining a Drosophila Promoter for Directing Expression to the Nervous System," *J. Neurochem.* 63(1): 41-51 (1994), which is hereby incorporated by reference in its entirety), a MAP-1B promoter (Liu et al., *Gene* 171:307-08 (1996), which is hereby incorporated by reference in its entirety), or a GAP-43 promoter. See U.S. Pat. No. 6,245,564 to Goldman et. al., which is hereby incorporated by reference in its entirety.

Having selected a promoter specific for the cell of interest, a nucleic acid molecule encoding a protein marker, preferably a green fluorescent protein under the control of the promoter is introduced into a plurality of cells to be sorted. The isolated nucleic acid molecule encoding a green fluorescent protein can be deoxyribonucleic acid (DNA) or ribonucleic acid (RNA, including messenger RNA or mRNA), genomic, recombinant, or mutant, biologically isolated or synthetic as described in U.S. Patent Application Publication No. 20040029269 to Goldman, which is hereby incorporated by reference in its entirety. Other suitable marker proteins include lacZ/beta-galactosidase or alkaline phosphatase.

Standard techniques are then used to place the nucleic acid molecule encoding the marker protein under the control of the chosen cell specific promoter. Generally, this involves the use of restriction enzymes and ligation.

The resulting construct, which comprises the nucleic acid molecule encoding the marker protein under the control of the selected promoter (itself a nucleic acid molecule) (with other suitable regulatory elements if desired), is then introduced into a plurality of cells which are to be sorted and then sorting. Techniques for introducing the nucleic acid molecules of the construct into the plurality of cells and then sorting the cells are described in U.S. Patent Application Publication No. 20040029269 to Goldman et al., which is hereby incorporated by reference in its entirety.

Once the nucleic acid molecule encoding the marker protein is introduced into a plurality of cells, the promoter which controls expression of the marker protein only functions in the cell of interest. Therefore, the marker protein is only expressed in the cell of interest and those cells can be identified from among the plurality of cells by the expression of the marker protein (e.g. fluorescence of the GFP using any suitable means of fluorescent detection). For GFP, cells may be identified using epifluorescence optics, and can be physically picked up and brought together by Laser Tweezers (Cell Robotics Inc., Albuquerque, N. Mex.). Alternatively, the cells can be separated in bulk through fluorescence activated cell sorting, a method that effectively separates the fluorescent cells from the non-fluorescent cells.

As an alternative to using promoter-based cell sorting to recover glial progenitor cells from the mixed population, an immunoseparation procedure can be utilized. In a positive immunoselection technique, the desired cells (i.e. glial progenitor cells) are isolated based on proteinaceous surface markers naturally present on the progenitor cells. For example, the surface marker A2B5 is an initially expressed early marker. See Nunes et al., "Identification and Isolation of Multipotential Neural Progenitor Cells from the Adult Human White Matter," *Soc. Neurosci. Abstr*. (2001), which is hereby incorporated by reference in its entirety. Using an antibody specific to that marker, glial progenitor cells can be separated from a mixed population of cell types.

Alternatively, or in combination with the positive immunoselection method described above, a mixed cell population can be depleted of undesirable cell types, leaving the desired cell population. This method involves separating cells based on proteinaceous surface markers that are specific to cell populations other than the glial progenitor cells (i.e. neuronal cells, endothelial cells, etc.) and retaining the glial progenitor cell population.

Cell specific antibodies for immunoseparation techniques can be labeled with a fluorescent, biotin, or hapten label to facilitate separation of cells to which they bind. Alternatively, the antibodies can be attached to paramagnetic beads so that cells which bind to the beads through the attached antibodies can be recovered by a biomagnetic separation process. Any other suitable method for cell separation known in the art, including attachment to and disattachment from solid phase (i.e.immunopanning), is also within the scope of the present invention The glial progenitor cells can be transplanted bilaterally into multiple sites of the non-mammal host animal. Methods for transplanting nerve tissues and cells into host brains are described by Bjorklund and Stenevi (eds), *Neural Grafting in the Mammalian CNS*, Ch. 3-8, Elsevier, Amsterdam (1985); U.S. Pat. No. 5,082,670 to Gage et al.; and U.S. Pat. No. 6,497,872 to Weiss et al., which are hereby incorporated by reference in their entirety. Typical procedures include intraparenchymal, intracallosal, intraventricular, intrathecal, and intravenous transplantation.

Intraparenchymal transplantation is achieved by injection or deposition of tissue within the host brain so as to be apposed to the brain parenchyma at the time of transplantation. The two main procedures for intraparenchymal transplantation are: 1) injecting the donor cells within the host brain parenchyma or 2) preparing a cavity by surgical means to expose the host brain parenchyma and then depositing the graft into the cavity (Bjorklund and Stenevi (eds), *Neural Grafting in the Mammalian CNS*, Ch. 3, Elsevier, Amsterdam (1985), which is hereby incorporated by reference in its entirety). Both methods provide parenchymal apposition between the donor cells and host brain tissue at the time of grafting, and both facilitate anatomical integration between the graft and host brain tissue. This is of importance if it is required that the donor cells become an integral part of the host brain and survive for the life of the host.

Glial progenitor cells can also be delivered intracallosally as described in U.S. Patent Application Publication No. 20030223972 to Goldman. The glial progenitor cells can also be delivered directly to the forebrain subcortex, specifically into the anterior and posterior anlagen of the corpus callosum. Glial progenitor cells can also be delivered to the cerebellar peduncle white matter to gain access to the major cerebellar and brainstem tracts. Glial progenitor cells can also be delivered to the spinal cord.

Alternatively, the cells may be placed in a ventricle, e.g. a cerebral ventricle. Grafting cells in the ventricle may be accomplished by injection of the donor cells or by growing the cells in a substrate such as 30% collagen to form a plug of solid tissue which may then be implanted into the ventricle to prevent dislocation of the graft cells. For subdural grafting, the cells may be injected around the surface of the brain after making a slit in the dura.

In one embodiment, a candidate agent is administered to the non-human mammal prior to, concurrent with, or after infection. It is then assessed whether the candidate agent therapeutically modifies the in vivo human glial cell response to the pathogen.

Candidate agents may be obtained from a wide variety of sources including libraries of synthetic or natural compounds. For example, numerous means are available for random and directed synthesis of a wide variety of organic compounds and biomolecules, including expression of randomized oligonucleotides, synthetic organic combinatorial libraries, phage display libraries of random or non-random polypeptides, combinatorial libraries of proteins or antibodies, and the like. Alternatively, libraries of natural compounds in the form of bacterial, fungal, plant, and animal extracts are available or readily produced. Additionally, natural and synthetically produced libraries and compounds can be readily modified through conventional chemical, physical, and biochemical means. Further, known agents may be subjected to directed or random chemical modifications such as acylation, alkylation, esterification, amidification, etc. to produce structural analogs of the agents.

Candidate agents of the present invention can be administered via any standard route of administration known in the art, including, but not limited to, parenteral (e.g., intravenous, intraarterial, intramuscular, subcutaneous injection, intrathecal), oral (e.g., dietary), topical, transmucosal, or by inhalation (e.g., intrabronchial, intranasal or oral inhalation, intranasal drops).

Candidate agents of the present invention are formulated in accordance with their mode of administration. For oral administration, for example, the candidate agents of the present invention are formulated into an inert diluent or an assimilable edible carrier, enclosed in hard or soft shell capsules, compressed into tablets, or incorporated directly into food. Agents of the present invention may also be administered in a time release manner incorporated within such devices as time-release capsules or nanotubes. Such devices afford flexibility relative to time and dosage. For oral therapeutic administration, the agents of the present invention may be incorporated with excipients and used in the form of tablets, capsules, elixirs, suspensions, syrups, and the like. Such compositions and preparations should contain at least 0.1% of the agent, although lower concentrations may be effective and indeed optimal. The percentage of the agent in these compositions may, of course, be varied and may conveniently be between about 2% to about 60% of the weight of the unit. The amount of an agent of the present invention in such therapeutically useful compositions is such that a suitable dosage will be obtained.

Also specifically contemplated are oral dosage forms of the agents of the present invention. The agents may be chemically modified so that oral delivery of the derivative is efficacious. Generally, the chemical modification contemplated is the attachment of at least one moiety to the component molecule itself, where said moiety permits inhibition of proteolysis and uptake into the blood stream from the stomach or intestine. Also desired is the increase in overall stability of the component or components and increase in circulation time in the body. Examples of such moieties include: polyethylene glycol, copolymers of ethylene glycol and propylene glycol, carboxymethyl cellulose, dextran, polyvinyl alcohol, polyvinyl pyrrolidone and polyproline (Abuchowski and Davis, "Soluble Polymer-Enzyme Adducts," In: *Enzymes as Drugs*, Hocenberg and Roberts, eds., Wiley-Interscience (1981), which is hereby incorporated by reference in their entirety). Other polymers that could be used are poly-1,3-dioxolane and poly-1,3,6-tioxocane. Preferred for pharmaceutical usage, as indicated above, are polyethylene glycol moieties.

The candidate agents of the present invention may also be delivered systemically, formulated for parenteral administration by injection, e.g., by bolus injection or continuous infusion. Solutions or suspensions of the agent can be prepared in water suitably mixed with a surfactant such as hydroxypropylcellulose. Dispersions can also be prepared in glycerol, liquid polyethylene glycols, and mixtures thereof in oils. Illustrative oils are those of petroleum, animal, vegetable, or synthetic origin, for example, peanut oil, soybean oil, or mineral oil. In general, water, saline, aqueous dextrose and related sugar solution, and glycols, such as propylene glycol or polyethylene glycol, are preferred liquid carriers, particularly for injectable solutions. In all cases, the form must be sterile and must be fluid to the extent that easy syringability exists. It must be stable under the conditions of manufacture and storage and must be preserved against the contaminating action of microorganisms, such as bacteria and fungi.

Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents.

Intraperitoneal or intrathecal administration of the agents of the present invention can also be achieved using infusion pump devices such as those described by Medtronic, Northridge, Calif. Such devices allow continuous infusion of desired compounds avoiding multiple injections and multiple manipulations.

In addition to the formulations described previously, the agents may also be formulated as a depot preparation. Such long acting formulations may be formulated with suitable polymeric or hydrophobic materials (for example as an emulsion in an acceptable oil) or ion exchange resins, or as sparingly soluble derivatives, for example, as a sparingly soluble salt.

Effective doses of the candidate agents of the present invention may vary depending upon many different factors including mode of administration, target site, physiological state of the patient, other medications or therapies administered, and physical state of the patient relative to other medical complications. Treatment dosages need to be titrated to optimize safety and efficacy.

The step of assessing may involve determining the behavior or fate of the human glial cells using a metric selected from the group consisting of morphology, immunophenotype, transcriptionally-regulated reporters, gene expression profiles, mitotic rate, mitotic fraction, metabolic rate, mitochondrial function, oxidative state, telomerase activity, apoptotic index, or net cell survival.

When assessing involves examining cellular morphology, the assessment can include measurements of the cell size, fiber outgrowth, length, complexity, or indices of myelination efficiency (e.g. G-ratio, axonal ensheathment efficiency, proportion of axons myelinated, number of axons myelinated per oligodendrocyte, and number of myelin wraps per axon). Such measurements can be carried out using standard neurohistological techniques known in the art. Typically, such analyses include examining various sections of brain tissue that have been processed according to the histological method employed and labeled with one or more cell specific or nucleic acid markers to aid in examination and measurements. Measurements can be performed using brightfield or fluorescent microscopy, confocal microscopy, or electron microscopy depending on the particular endpoint to be measured.

When the assessing step involves examining immunophenotype, such as an increase or decrease in cell specific gene expression, immunocytochemical, immunoblotting, flow cytometry, or fluorescence-activated cell sorting techniques can be used to measure immunophenotype. The specific cellular protein, RNA, or DNA to be assessed (i.e. receptor, enzyme, signaling protein, etc.) will depend on the endpoint being investigated (i.e. stroke, injury, therapeutic agent, toxicant).

Likewise, when the assessing step includes the examination of gene expression profiles to determine an increase or decrease in cell specific gene expression, microarrays, real-time PCR, or protein expression profiling techniques readily known in the art can also be employed. U.S. Patent Application No. US20050176626 to Goldman et al., which is hereby incorporated by reference in its entirety, describes methods for assessing gene expression in human white matter progenitor cells and provides a comprehensive list of gene targets, which can be adapted for use in the methods of the present invention.

If the step of assessing includes examining transcriptionally-regulated reporters, promoter/enhancer-driven reporters in enzymatic or fluorescent form are utilized.

When the assessing step includes examining mitochondrial function, any one of a variety of assays known in the art to examine mitochondrial function or integrity can be employed. For example, mitochondrial metabolic activity can be measured using methods described by Springer et al., "A Rapid and Sensitive Assay for Measuring Mitochondrial Metabolic Activity in Isolated Neural Tissue," *Brain Research Protocol* 2(4):259-263 (1998), which is hereby incorporated by reference in its entirety can be utilized. Alternatively, the rate of oxygen consumption as an indicator of mitochondrial function can be measured as described by Will et al., "Analysis of Mitochondrial Function Using Phosphorescent Oxygen-Sensitive Probe," *Nature Protocols* 1:2563-72 (2007), which is hereby incorporated by reference in its entirety, can also be employed. Additionally, there are various commercially available dyes and stains, which are specific for visualizing and measuring mitochondria viability (Invitrogen, Carlsbad, Ca). Alternatively, mitochondrial specific gene expression can be examined as a measure of mitochondrial function.

If the assessing step includes examining apoptosis, it is preferable that a variety of apoptotic endpoints are examined. Such endpoints include an assessment of the nucleus, specifically, fragmentation of chromatin, degradation of the nuclear envelope and nuclear blebbing. Several nucleic acid stains are known in the art and are commercially available to facilitate the detection of DNA integrity as a measure of apoptosis by fluorescence imaging or flow cytometry. Other indices of apoptosis to be measured include cellular permeability, caspase enzyme activity (Slee et al., *Cell Death Differ* 6:1067-74 (1999); Linca L F, *Immunol. Cell Biol.* 76:1-19 (1998), which are hereby incorporated by reference in their entirety), externalization of phosphatidylserine (van Engeland et al., *Cytometry* 31:1-9 (1998), which is hereby incorporated by reference in its entirety), disruption of mitochondria, including changes in the membrane potential and alteration to the oxidation-reduction potential (Finkel E., *Science* 292:624-626 (2001); Brenner et al., *Science* 289: 1150-1151 (2000); Desagher et al., *Trends Cell Biol.* 10:369-377 (2000), which are all hereby incorporated by reference in there entirety), and significant alterations in levels of intracellular ions or the ratio of ATP to ADP.

Another embodiment of the present invention relates to a method of identifying an agent suitable for treating or inhibiting a pathogenic brain infection. This method involves providing a non-human mammal with at least 30% of its glial cells in its corpus callosum being human glial cells and/or with at least 5% of its glial cells in its brain and brain stem white matter being human glial cells, and providing a candidate agent. The non-human mammal is exposed to an infective brain pathogen under conditions effective to establish a brain infection, and the candidate agent is administered to the non-human mammal prior to, concurrent with, or after exposing. As a result of administering, one or more indices of pathogenic brain infection are assessed to identify an agent suitable for treating or inhibiting the pathogenic brain infection.

The non-human mammal, pathogens, candidate agents, as well as methods of administering are described above. Assessing indices of brain infection has the same characteristics as the assessing step described above.

Yet another embodiment of the present invention relates to a non-human mammal with at least 30% of all of its glial cells in its corpus callosum being human glial cells and/or at least 5% of all of its glial cells in the white matter of its brain and/or brain stem being human glial cells, wherein the non-human mammal has a pathogenic brain infection.

The non-human mammal as well as pathogens are described above.

EXAMPLES

The following examples are provided to illustrate embodiments of the present invention but they are by no means intended to limit its scope.

Materials and Methods for Examples 1-10

Tissue Preparation.

Human fetal brain tissue was obtained from aborted fetuses (16-22 weeks g.a.) under protocols approved by the University of Rochester-Strong Memorial Hospital Research Subjects Review Board. Briefly, cortical tissues were minced and dissociated using papain and DNAase as described (Roy et al., in *Myelin Biology and Disorders*, R. Lazzarini, Ed. (Elsevier, Amsterdam, 2004), pp. 259-287, which is hereby incorporated by reference in its entirety), always within 2 hours of extraction. The dissociates were maintained overnight in DMEM/F12/N1-based medium supplemented with 10 ng/ml FGF2 (Windrem et al., "Fetal and Adult Human Oligodendrocyte Progenitor Cell Isolates Myelinate the Congenitally Dysmyelinated Brain," *Nature Med.* 10:93-97 (2004); Keyoung et al., "High-yield Selection and Extraction of Two Promoter-Defined Phenotypes of Neural Stem Cells From the Fetal Human Brain," *Nature Biotech.* 19:843-850 (2001), which are hereby incorporated by reference in their entirety).

Cell Isolation.

GPCs were obtained by immunomagnetic sorting (MACS, Miltenyi) for either the phenotype A2B5+/PSA-NCAM−, by serial immunodepletion of PSA-NCAM and immunoselection of A2B5 (Windrem et al., "Neonatal Chimerization with Human Glial Progenitor Cells Can Both Remyelinate and Rescue the Otherwise Lethally Hypomyelinated Shiverer Mouse," *Cell Stem Cell* 2:553-565 (2008), which is hereby incorporated by reference in its entirety), or for the more specific CD140a/PDGFαR+ phenotype, the latter using anti-human CD140a (BD) followed by anti-mouse IgG2a+b microbeads (Miltenyi) (Sim et al., "CD140a Identifies a Population of Highly Myelinogenic, Migration-Competent and Efficiently Engrafting Human Oligodendrocyte Progenitor Cells," *Nature Biotech.* 29:934-941 (2011), which is hereby incorporated by reference in its entirety). A2B5+/PSA-NCAM-cells were used for all in vivo experiments, while in vitro experiments were done primarily with CD 140a+ cells; the latter comprise the fraction of A2B5+/PSA-NCAM-cells that includes all potentially oligoneogenic glial progenitors, while largely excluding committed astroglia. After MACS isolation, the cells were maintained in DMEM/F12/N1 supplemented with 20 ng/ml PDGF and 10 ng/ml FGF-2, and transplanted into the brains of neonatal mice within three days of sorting. For preparing specific phenotypes, GPCs were obtained by CD140a/PDGFαR sorting, while oligodendroglia were then derived from these GPCs by culture for one week in triiodothyronine and IGF1-supplemented media (Sim et al., "CD140a Identifies a Population of Highly Myelinogenic, Migration-competent and Efficiently Engrafting Human Oligodendrocyte Progenitor Cells," *Nature Biotech.* 29:934-941 (2011); Holmseth et al., "Specificity Controls for Immunocytochemistry: The Antigen Preadsorption Test Can Lead to Inaccurate Assessment of Antibody Specificity," *The J. Histochem. and Cytochem.* 60:174-187 (2012), which are hereby incorporated by reference in their entirety). Astrocytes were isolated from the tissue dissociates using MACS targeting the astroglial hyaluronate receptor CD44 (Liu et al., "CD44 Expression Identifies Astrocyte-Restricted Precursor Cells," *Dev. Biol.* 276:31-46 (2004), which is hereby incorporated by reference in its entirety), using conjugated microbeads (Miltenyi) according to the manufacturer's instructions.

Viral Construction, Production and Purification.

JCV type 1A rearranged NCCR genome (Mad-1; GenBank NC_001699) in the Bluescript plasmid vector was a kind gift of Dr. Richard Frisque. Type 2A VP1 archetype NCCR JCV genome ("type 2A archetype"; GenBank accession # AY121915) was synthesized in three fragments (GeneArt), and subsequently ligated to yield the full-length JCV 2A archetype genome, cloned in an *E. coli* replicon. To create type 2A rearranged viral genome, JCV 2A archetype NCCR was replaced with rearranged NCCR of Mad1, by exchanging a 416 bp Nco1 fragment from the archetype genome, with 425 bp Nco1 fragments of pBS-Mad-1. Site-directed mutagenesis (QuikChange, Agilent Technologies) was performed on this rearranged 2A vector, to incorporate the VP1 mutations L55F (type 2A 55F VP1 virus), K60E (type 2A 60E VP1 virus), or S269F (type 2A 269F VP1 virus). To produce virus, viral genomes were excised from their corresponding replication plasmids with EcoRI restriction endonuclease digestion. The linearized viral genomes were recircularized in a dilute ligation reaction (5 μg/ml) at room temperature overnight, ethanol precipitated and resuspended in TE, and transfected into 293FT cells (Invitrogen) with FuGeneHD (Roche). Cells were split into 20×T160 flasks in a week, and 2 weeks later the cultures were collected for virus purification. During these last 2 weeks of virus production, culture medium was added to cultures rather than replaced. Supernatant was cleared at 3000 RPM for 20 min, and the pellet then re-suspended in 1/20 original volume and used for virus purification. The re-suspended pellet was freeze-thawed 3 times to disrupt cells, followed by treatment with benzonase (250 u/ml) (Sigma) and neuraminidase (20 U/ml) (NEB) at 37° C. for 3 hrs, to aid in dissociation of viral particles from cellular debris. At that point, detergents including 0.1% deoxycholate and 0.5% TritonX-100 were added, and incubation continued for another hour. The resultant suspension was spun at 3000 RPM for 30 min at 4° C., the pellet discarded, and the supernatant loaded onto 30% sucrose in low salt buffer (10 mM HEPES pH 7.9; 1 mM $CaCl_2$; 1 mM MgCl2; 5 mM KCl), then centrifuged using a SW28 rotor at 28,000 RPM for 3 hrs. at 4° C. The resultant pellet was soaked in high salt buffer (10 mM HEPES pH7.9; 1 mM $CaCl_2$; 1 mM $MgCl_2$; 5 mM KCl; 0.8 M NaCl) overnight, then re-suspended and re-spun through 30% sucrose. The final pellet was again soaked overnight in high salt buffer, re-suspended, and then aliquoted and frozen at −80° C. Final JCV preparations were in the range of $1.6\times10^{12}$-$2.2\times10^{13}$ GE/ml.

Viral Sequencing.

The forebrain hemisphere of each brain contralateral to that used for histological analysis was cut into 12×1 mm thick coronal sections. DNA was then isolated from each slice using RecoverAll™ Total Nucleic Acid Isolation Kit for FFPE Tissues (Life Technologies), and the isolated DNA used for qPCR with JCV specific primer probe sets. 100 ng of total DNA from the second, fourth and ninth sections were amplified using the Herculase II Fusion Enzyme system (Cat 600677; Agilent Technologies). The VP1 coding region was amplified using full-length VP1 specific primers: 5' CCTCAATGGATGTTGCCTTT 3' (SEQ ID NO: 1) and 5' AAAACCAAAGACCCCTC (SEQ ID NO: 2). PCR amplification products were then cloned using the TOPO TA Cloning Kit (Invitrogen), transformed and plated according to manufacturer's specifications. Thirty two individual colonies for each cloned product (96 colonies per each brain) were then screened and sequenced, using an Applied Biosystems 3730XL DNA Analyzer with BigDye Terminator v. 3.1 chemistry. As a control, 100 ng of viral DNA (Mad-1) prepared from the same virus injected into that mouse brain were amplified and cloned using the same conditions as the DNA prepared from brain tissue (in this, H122Y and H122P mutations were noted, relative to mad1A archetype). 96 individual colonies were sequenced, to allow us to estimate the mutation rate of the starting viral genotype. Coding mutations were identified after translating the DNA sequence and aligning the predicted protein sequence to that of Mad-1.

Tissue Collection.

Litters of shiverer/$rag2^{-/-}$ mice, which had been transplanted neonatally with human cells, were injected with Mad-1 virus between the ages of 9 and 16 weeks. Homozygous shi/shi×$rag2^{-/-}$ mice in the colony do not reliably live longer than 20-22 weeks. Accordingly, when infected mice were noted to be moribund, they were euthanized with sodium pentobarbital (Nembutal) and transcardially perfused with HBSS followed by 4% PFA/PB. The brains were then extracted from the skull, post-fixed for 2 hours in the same fixative, cryoprotected in a sucrose buffer. Serial sagittal sections were cut at 14 μm on a cryostat (Leica) and mounted on glass slides. Myelin wild-type $rag1^{-/-}$ mice were injected with JCV at 16 weeks and sacrificed at 28 weeks of age.

Infection In Vitro.

CD140a/PDGFαR+ GPCs and CD44+ astrocytes were plated at 5,000 cells/cm2 on Permanox chamber slides (Thermo) coated with poly-L-ornithine (Sigma Aldrich) plus laminin (BD) or 12-mm coverslips coated with Matrigel (33 μg/ml, BD). OPCs were allowed to differentiate into oligodendrocytes for 7 days in Neurobasal medium (Invitrogen) supplemented with 1×B27 and 30 ng/ml T3, 10 ng/ml IGF-1, and 10 ng/ml NT-3. The cells were infected with JCV in 250 μl of medium at $10^5$ genomic equivalents (GE) per cell for 2 hours at 37° C. CD44+MACS-derived astrocytes were maintained in the DMEM/F12/N1 based medium with 1% platelet-depleted FBS and infected 2 days after plating at $10^5$ GE/cell. CD140+MACS-derived GPCs were plated in ultralow binding 24-well plates (Corning) at $10^5$ cells/well in Neurobasal medium supplemented with 1×B27, 20 ng/ml PDGFAA, and 10 ng/ml FGF-2. The following day, the cells were infected with JCV at $10^5$ GE/cell for 2 hrs.

Animals and GPC Transplantation.

Two immunodeficient mouse strains were used in this study, one myelin-deficient and the other normally myelinated. Homozygous myelin-deficient shiverer mice (shi/shi) were crossed with homozygous rag2−/− immunodeficient mice (Taconic, Hudson, N.Y.) to generate a line of shi/shi× rag2−/− myelin-deficient and immunodeficient mice. In addition, normally myelinated rag1−/− immunodeficient mice were obtained from the Jackson Laboratory (Bar Harbor, Me.). All mice were bred and housed in a pathogen-free environment in accordance with the University of Rochester animal welfare regulations. Newborn pups were transplanted within a day of birth, with 200,000-400,000 donor cells delivered across four injection sites (Windrem et al., "Neonatal Chimerization With Human Glial Progenitor Cells Can Both Remyelinate and Rescue the Otherwise Lethally Hypomyelinated Shiverer Mouse," *Cell Stem Cell* 2:553-565 (2008), which is hereby incorporated by reference in its entirety).

Virus Administration.

Adult mice were anesthetized with a mixture of ketamine and xylazine, in accordance with University of Rochester protocols. JCV, prepared as noted to a final concentration of $1.6\times10^{12}$-$2.2\times10^{13}$ GE/ml, was thawed and resuspended in HBSS buffer before injection. One μL of virus was injected bilaterally into the corpus callosum (total 2 μl; coordinates AP: +0.5: ML: ±0.8: DV: −1.4), using a Gastight (Hamilton) syringe.

Immunocytochemistry in Culture.

Adherent cells were fixed with 4% PFA/PB and immunolabeled using primary antibodies as follows: mouse anti-T-Ag antibody (1:300, Pab2003, gift of R. Frisque, Pennsylvania State University); mouse anti-large T-Ag antibody (1:50, Pab416, Calbiochem): rabbit anti-SV40 T-Ag antibody (1:50, v-300, SantaCruz; known to cross react with JCV T-Ag); mouse anti-VP1 antibody (1:3000, Pab 597; obtained from Biogen); chicken anti-GFAP antibody (1:800, Chemicon); rabbit anti-PDGFαR antibody (1:800, D13C6, Cell Signaling Technology); mouse anti-phosphorylated p53 (Ser15) antibody (1:100, Cell Signaling Technology); rabbit anti-cyclin B1 antibody (1:180, Cell Signaling Technology); rabbit anti-Ki67 antibody (1:300, Thermo). Oligodendrocytes were stained as live cells with supernatant from 04 hybridoma (gift of I. Duncan, Univ. of Wisconsin) at 10 μg/ml, followed by fixation with 4% paraformaldehyde (PFA)/0.1 M phosphate buffer (PB). $CD140a^+$ GPCs were collected as spheres, fixed with 2% PFA/PB for 10 minutes, immersed in 15% sucrose/PB then 30% sucrose/PB, cut at 6 m on a cryostat, mounted on glass slides, and subjected to immunocytochemistry. Alexa Fluor 488, 594 and 647 conjugated goat secondary antibodies against appropriate animal species and immunoglobulin classes (Invitrogen) were used at 1:1000. The nucleus was counterstained with DAPI at 600 nM.

Immunocytochemistry in Sections.

Slide mounted sections were rehydrated with 0.1 M phosphate-buffered saline (PBS) and permeabilized and blocked for 1 hr, with PBS containing 0.1% Triton X-100 and 10% normal goat serum. Immunolabeling was performed using the following primary antibodies: mouse anti-human nuclear antigen, clone 235-1 (1:800, MAB1281, Millipore), mouse anti-VP1 (1:1000, PAB597), rabbit anti-SV40 VP1 (1:500, AB53977, Abcam), mouse anti-T-TAg (1:60), rabbit anti-SV40 T-Ag, v-300 (1:50), rat anti-MBP (1:25, ab7349-1, Abcam), mouse anti-human GFAP SMI-211 (1:500, ADG 050809, Covance), rabbit anti-GFAP (1:800, ab33922-100, Abcam), mouse anti-human chondroitin sulfate proteoglycan (NG2, 1:200, MAb 2029, Millipore), rabbit anti-NG2 (1:200, AB5320), rabbit anti-Ki67 (1:50, clone SP6, LabVision), rabbit anti-PDGFRα (1:400). Alexa Fluor-conjugated secondary antibodies were used at 1:400 (Invitrogen). Slides were cover-slipped using Vectashield mounting media with DAPI (Vector Laboratories).

In Situ Detection of JCV Genome.

JCV infection was also detected by DNA in situ hybridization. The slides were incubated with a biotinylated DNA probe for the JCV genome (Enzo Life Sciences) at 2 μg/ml at 95° C. for 2 min, then at room temperature for 1 hour. The hybridization signal was detected by incubating with fluorescein-labeled avidin (1:400, Invitrogen).

Flow Cytometric Cell Cycle Analysis.

Fetal astrocytes were infected with type 2A VP1, Mad-1 NCCR JCV at $10^4$ GE/cell in 6-well plates, passaged twice in 60-mm dishes, then plated into 100-mm dishes. Fourteen days after inoculation, the cells were harvested using Accutase and fixed with 70% ethanol overnight at −20° C. The cells were immunolabeled with rabbit anti-T-Ag polyclonal antibody (v-300, SantaCruz, 1:500) followed by Alexa Fluor 488-conjugated secondary antibody (1:1,000). DNA content was detected with propidium iodide (4 μg/ml). Flow cytometry was performed using the FACS Canto (BD Biosciences) and data were analyzed with the FlowJo software (Tree Star, Ashland, Oreg.). The percentage of cells in each cell cycle was calculated based on the Dean-Jett-Fox model in FlowJo, comparing vehicle-treated and JCV-infected astrocytes.

Image Analysis.

The incidence of individual human phenotypes was estimated using the Optical Fractionator Program of Stereo Investigator (MBF Bioscience, Burlington, Vt.). Stained sagittal sections were imaged as 7-μm stacks of 7 superimposed optical slices, each taken at 0.2 μm intervals in the corpus callosum at 20×, using an Olympus BX51 with Ludl stage. The entire corpus callosum (excluding fimbria) was mapped for each of two random sections at either 336-672 μm or 672-1008 μm from the midline, for each experimental mouse.

Statistics.

Data are provided as means±SEM. All statistical analyses were performed using Prism (GraphPad Software, La Jolla, Calif.) and $p<0.05$ was considered as statistically significant.

Example 1

JCV Efficiently Infected Astroglia and their Progenitors in Culture

Figure 8:
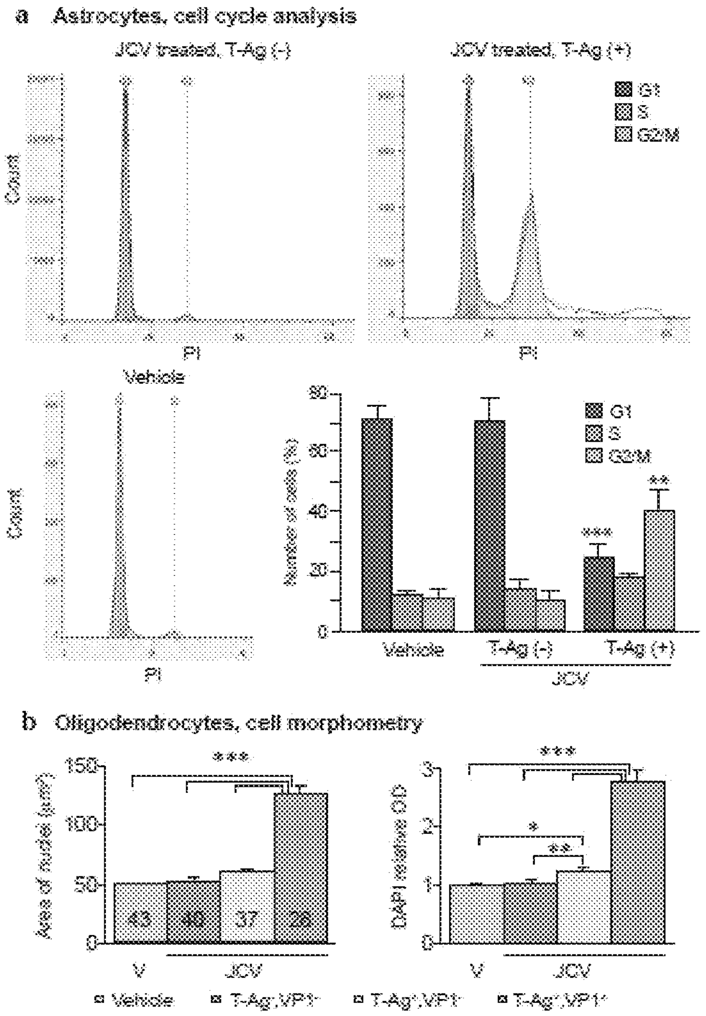
FIGS. 8A-B show JCV infected glia exhibited G2 cell cycle arrest.

Although PML has traditionally been viewed as a disease of oligodendrocytes, both astrocytic and glial progenitor infection have been reported in vitro (Major et al., "Human Fetal Astrocytes in Culture Support the Growth of the Neurotropic Human Polyomavirus, JCV," *J Neuropathol. Exp. Neurol.* 48:425-436 (1989); Monaco et al., "Progenitor-Derived Oligodendrocyte Culture System From Human Fetal Brain," *J. Vis. Exp.* e4274 (2012); Seth et al., "JC Virus Induces Nonapoptotic Cell Death of Human Central Nervous System Progenitor Cell-Derived Astrocytes," *Journal of Virology* 78:4884-4891 (2004); Radhakrishnan et al., "JC Virus-Induced Changes in Cellular Gene Expression in Primary Human Astrocytes," *J. Virol.* 77:10638-10644 (2003); Messam et al., "Lineage Pathway of Human Brain Progenitor Cells Identified by JC Virus Susceptibility," *Ann. Neurol.* 53:636-646 (2003), which are hereby incorporated by reference in their entirety). On that basis, it was first sought to assess the phenotypic selectivity of viral infection and propagation among the different phenotypes of human macroglia. To that end, either A2B5-directed immunoselection following PSA-NCAM depletion, or CD140a/PDGFαR-targeted selection, was used to isolate hGPCs from second trimester fetal human brain. The resultant isolates were then aliquoted, with some cultures maintained as hGPCs in serum-free media supplemented with FGF2 and PDGF, while others were switched to triiodothyronine to bias oligodendrocytic differentiation. In addition, CD44-based immunomagnetic sorting was used to select phenotypically-restricted astroglia from some samples. After at least a week in vitro, cultures of each phenotype were exposed to JCV. Both GPCs and astrocytes were infected quickly and efficiently by JCV, with robust expression within days of both the early viral T antigens (TAg) and the VP1 capsid protein (FIG. 1A-B). In contrast, oligodendrocytic infection in vitro was delayed and initially of relatively low efficiency (FIG. 1C). Of note, while VP1-defined viral replication was noticeably less common in oligodendroglia than in co-cultured astrocytes, with time in vitro, some VP-1+ oligodendroglia appeared as well (FIG. 1C-E). In astrocytes and oligodendrocytes alike, VP1− defined viral replication was associated with significant increments in nuclear size and DNA content (FIG. 8). Yet whereas cultured astrocytes continuously expanded and appeared to remain viable once infected, oligodendrocytes were postmitotic and rapidly died after infection. Together, these events resulted in the progressive accumulation of infected astroglia following initial infection.

Example 2

JCV Initially Infected Astroglia In Vivo

Since astrocytic infection was surprisingly more robust than that of oligodendrocytes in vitro, it was next sought to define the relative phenotype-selective tropism and infectivity of JCV in vivo. Since JCV infects only human glia, human glial chimeric mice were established so as to provide an in vivo model for JCV infection and JCV-dependent demyelination. To this end, neonatal immunodeficient and myelin-deficient shiverer mice (rag2−/−xMBPshi/shi) were injected with $2\times10^5$ human GPCs, delivered as $10^5$ cells/hemisphere in 2 intracallosal injections per side of $5\times10^4$ cells each. Myelination by neonatally-engrafted human GPCs has been well-characterized in these human glial chimeric mice, which first achieve dense callosal and capsular myelination only after 3 months of age (Windrem et al., "Neonatal Chimerization With Human Glial Progenitor Cells Can Both Remyelinate and Rescue the Otherwise Lethally Hypomyelinated Shiverer Mouse," *Cell Stem Cell* 2:553-565 (2008); Sim et al., "CD140a Identifies a Population of Highly Myelinogenic, Migration-Competent and Efficiently Engrafting Human Oligodendrocyte Progenitor Cells," *Nature Biotech.* 29:934-941 (2011), which are hereby incorporated by reference in their entirety). As a result, the effects of JCV in vivo in mice first injected with virus at 2, 3, or 4 months of age was assessed. At those time-points, Mad-1 (type 1A) JCV was delivered to the human glial chimeras, by stereotaxic intracallosal injection. The animals were then killed at 1, 2, or 3 months post-infection, and their brains assessed for both early and late JCV antigens, as well as for cellular pathology and myelin integrity.

Figure 2:
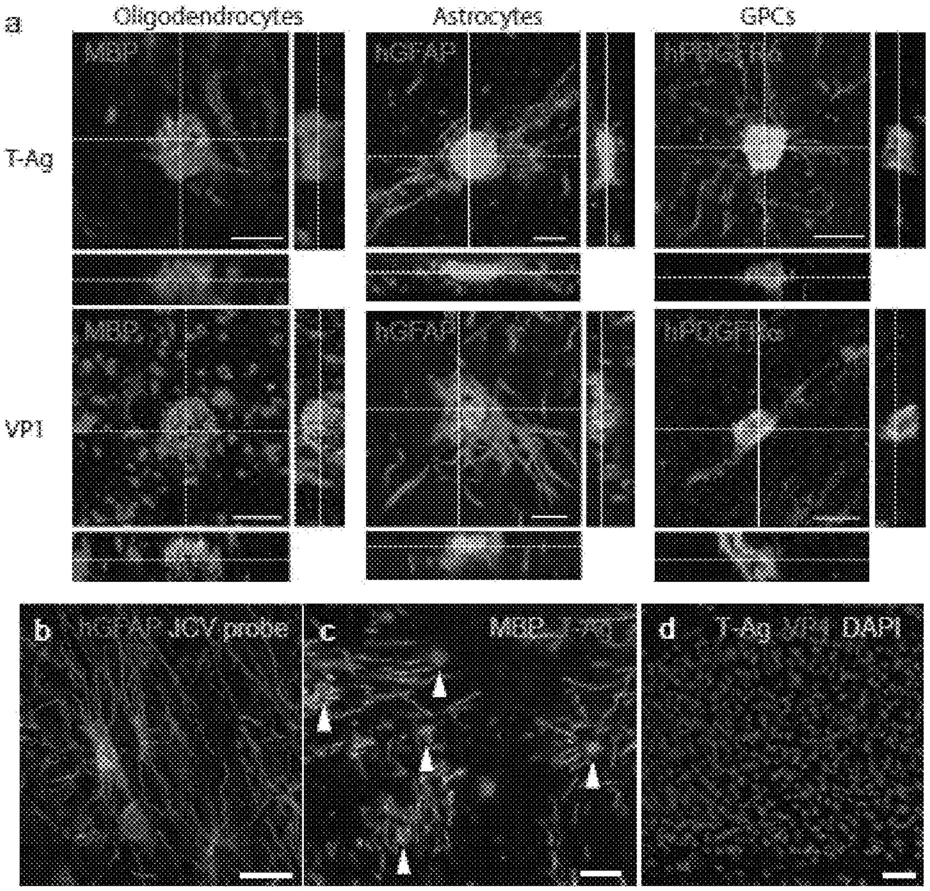
FIGS. 2A-D show JCV replicated more rapidly and efficiently in astroglia than oligodendrocytes in vivo. JCV induced the expression of the major early and late viral gene products, large T antigen (LgT) and VP1 capsid protein, respectively, throughout the human glial chimeric corpus callosum.
Figure 4:
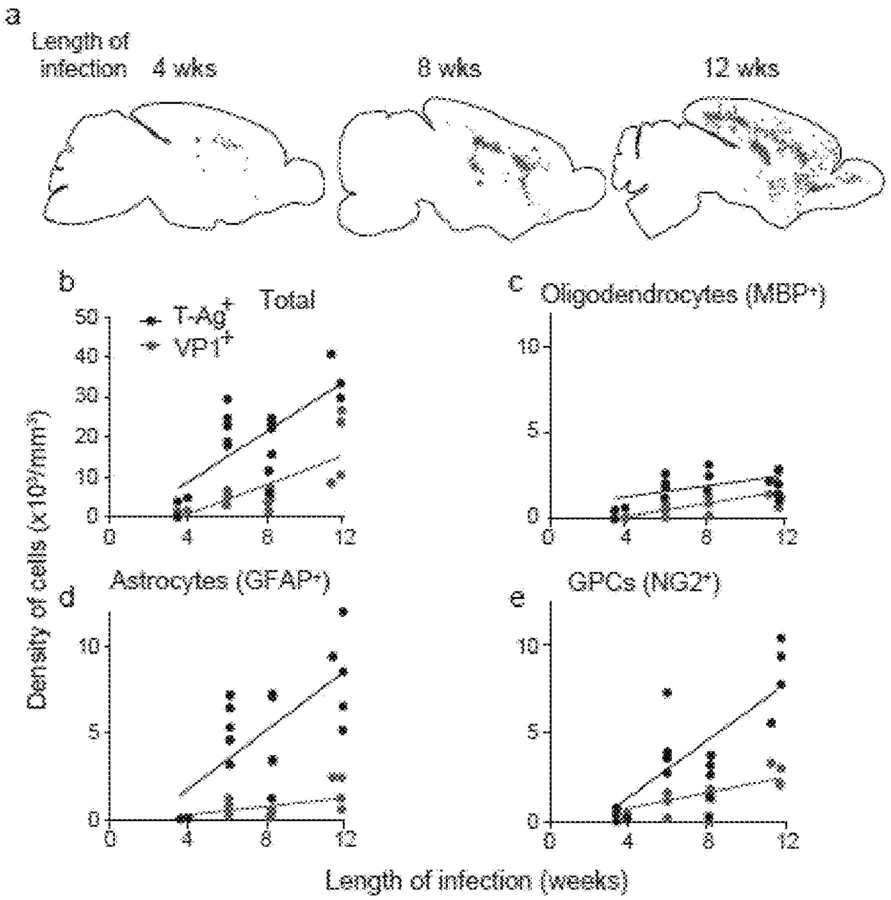
FIGS. 4A-E show viral propagation exhibited phenotype-selective spread. JC viral spread in vivo was tracked by immunostaining human glial chimeric shiverer brains for large T antigen and VP1, respectively, as a function of time after infection.

It was found that JCV induced the expression of the major early and late viral gene products, large T-antigen (LgT) and VP-1 capsid protein (VP1), respectively, and did so in oligodendrocytes, astrocytes, and GPCs throughout the chimeric corpus callosum (FIG. 2A). Infected astrocytes and GPCs were often magnocellular, with overtly enlarged nuclei, while processes of infected astrocytes manifested a bizarre fibrotic morphology (FIG. 2B), as described in human PML (Aksamit, Jr., A. J., "Progressive Multifocal Leukoencephalopathy: A Review of the Pathology and Pathogenesis," *Micro. Res. & Techniq.* 32:302-311 (1995), which is hereby incorporated by reference in its entirety). In contrast, at these early time-points, relatively few infected MBP+ oligodendroglia were noted, most of which expressed the early viral protein large T antigen rather than VP1, suggesting their infection without viral replication (FIG. 2C and FIG. 4C). Importantly, infection was restricted to human cells. No murine cells expressed either early or late viral genes, and non-chimeric unengrafted mouse controls manifested no evidence of infection after JCV injection (FIG. 2D).

Figure 3:
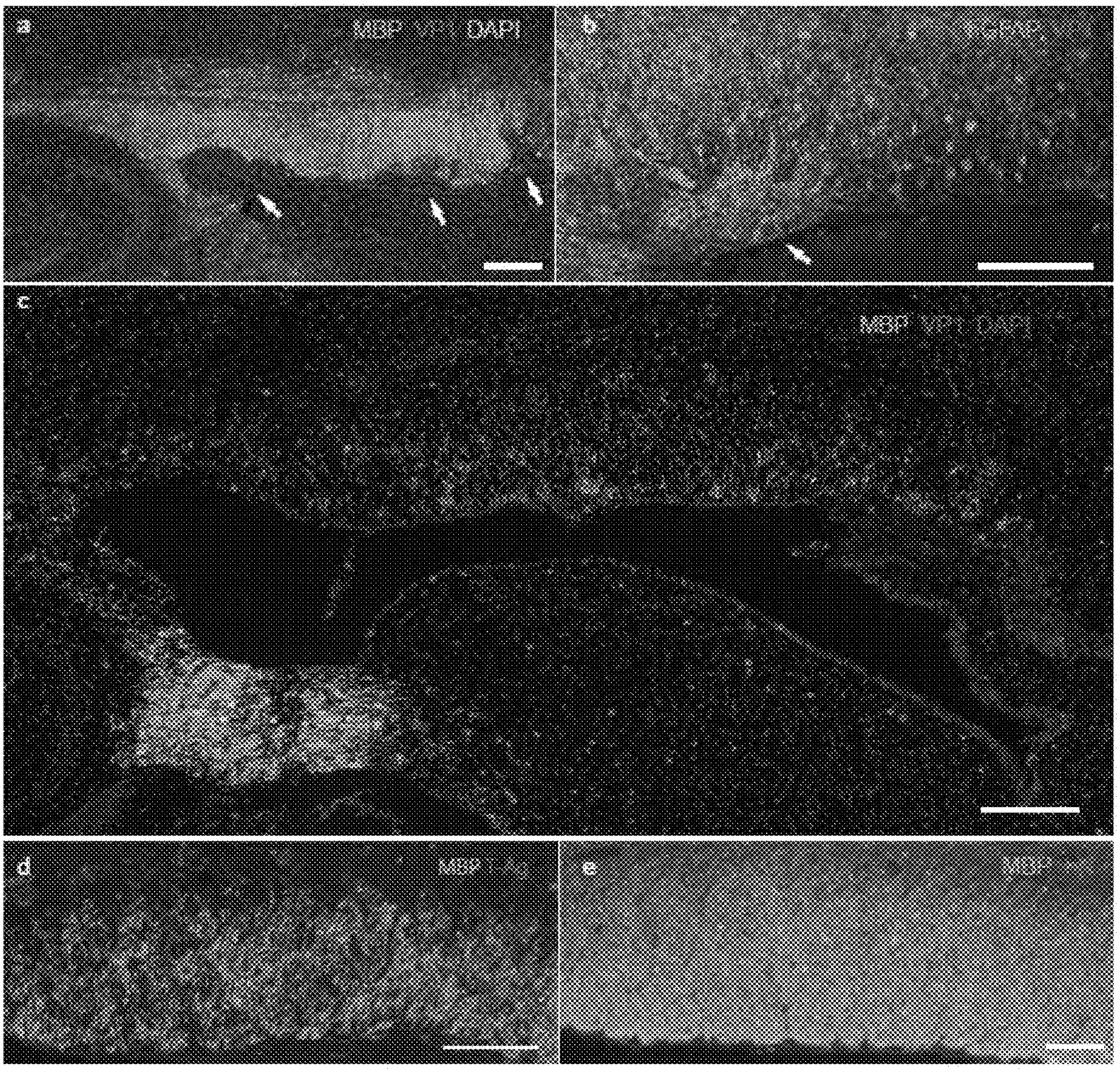
FIGS. 3A-E show JCV infection of human glial chimeras triggers both focal and diffuse demyelination.

At early sacrifice time-points, most infected cells appeared to be astrocytes and parenchymal progenitor cells. Indeed, abundant astrocytic infection appeared relatively quickly in injected regions, which were typically associated with regions of local demyelination and astrocytic hypertrophy in the callosal or fimbrial white matter (FIG. 3A-B). Indeed, despite ample evidence of dying and pyknotic MBP+ oligodendrocytes at later time points post-injection (FIG. 3C), relatively few VP1+ infected human oligodendrocytes were noted.

Example 3

JCV Infection In Vivo Resulted in Demyelination within Human Chimeric White Matter To better understand the means by which demyelination occurs in JCV infection, the patterns of demyelination noted in JCV-infected human glial chimeric brains were examined. By 4 weeks after JCV infection, focal regions of demyelination and infection-associated astrogliosis were noted in the forebrain white matter of infected mice, typically in discrete foci abutting the callosal wall of the lateral ventricle (FIG. 3A-B). Importantly, areas of demyelination were associated with dense aggregations of VP-1+ astrocytes. VP-1+ oligodendroglia were rare, despite overt oligodendrocytic loss and demyelination (FIG. 3A). By 12 weeks post-infection, demyelination was widespread and associated with regions of focal gliosis embedded within demyelinated loci. At these longer postinfection time-points, diffuse hypomyelination of the callosa and capsules of infected chimeric mice was noted (FIG. 3C-D). Oligodendrocytic VP1 expression remained unusual, but large T antigen immunolabeling revealed large numbers of infected oligodendrocytes (FIG. 3D). Human chimeric controls by that time point exhibited dense human GPC-derived myelination (FIG. 3E).

These observations suggest that the primary initial targets of JCV infection in the adult CNS are astrocytes and their progenitors, in that cellular expression of the VP1 capsid protein, which is expressed by mature post-replication virions, was largely limited to astroglia and GPCs. As such, these phenotypes may be the principal reservoirs for intracerebral viral propagation. In contrast, whereas VP-1+ infected human oligodendrocytes were uncommon, dying and pyknotic oligodendrocytes were abundant, many of which—though not all—expressed the early large T antigen. This observation suggests the initial infection of oligodendroglia, but their death or loss before the VP1− identified completion of viral replication.

Example 4

JCV Infection In Vivo Spreads in Different Cell Types at Different Rates

As a result of the human-selective nature of JCV infection, and the lack of early or phenotype specific radiographic surrogates, the dynamics of viral propagation in the infected CNS remain unknown. Thus, the pattern of JCV spread in human glial chimeras was investigated, as a function of time after infection. To this end, the expansion and spread of both infected glia, and of the fraction harboring replicating virus, was tracked by immunostaining for T-antigen and VP1 respectively. Both LgT+ and VP1+ human cells were progressively more numerous and widespread as a function of time after infection, with infection progressing from the site of viral injection to include much of the central white matter over a 4-12 week period (FIG. 4A). Notably, despite ample evidence of astrocytic viral replication as defined by VP1 expression by astrocytes and progenitors alike (FIG. 4B, FIG. 4D-E), a high proportion of LgT+ infected glia remained viable but VP1-negative. While these LgT+/VP1− infectants included oligodendrocytes, most were astroglial. Both the absolute number and relative proportions of infected oligodendrocytes were substantially lower than that of both astrocytes and GPCs. At all timepoints (FIG. 4C-E). Together, these data indicated that JCV infection and replication were less robust in oligodendroglia than in astrocytes, and that the latter proved more efficient as vehicles for viral spread. As post-mitotic cells, oligodendrocytes might then be merely the victims of JCV infection, and not significant contributors to viral propagation and spread.

Example 5

JCV does not Require Oligodendrocytes for Viral Infection and Spread

Figure 5:
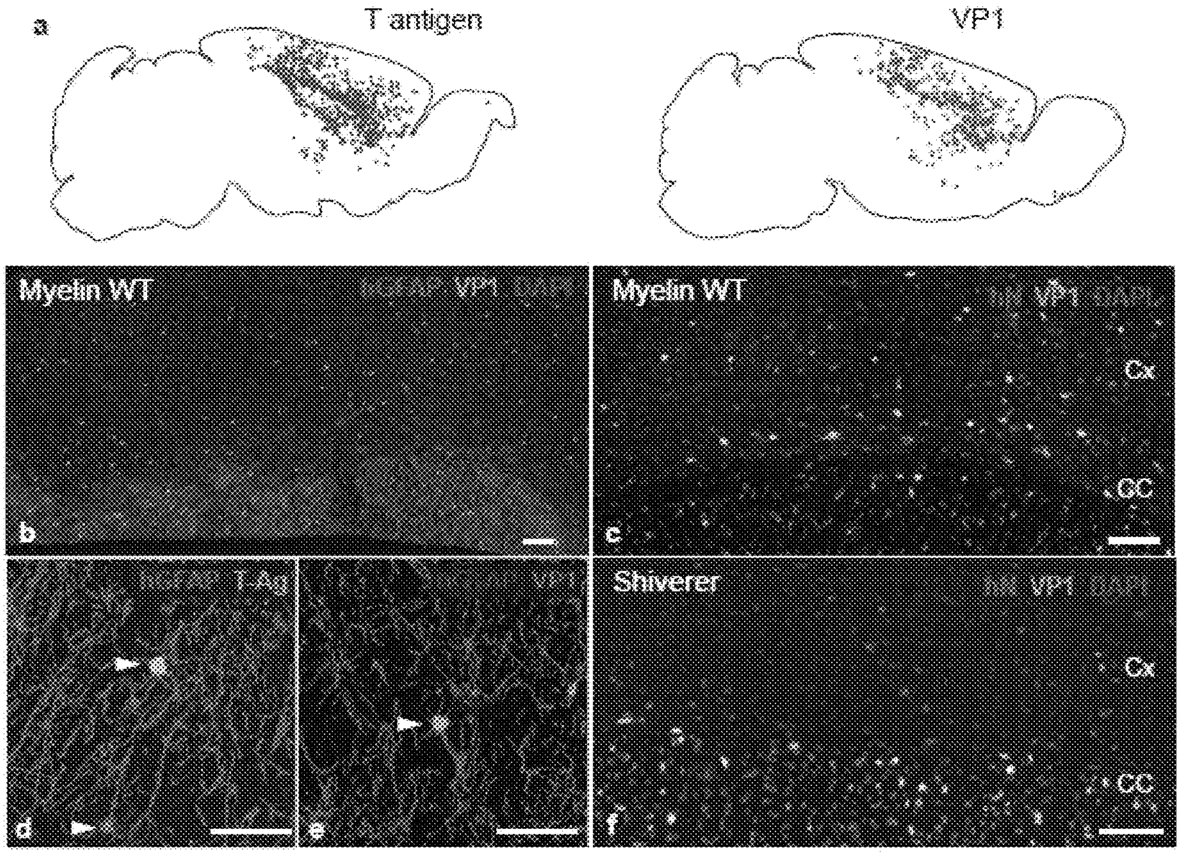
FIGS. 5A-F show astrocytes and GPCs are sufficient to support viral replication and spread in vivo.

Since astroglia appeared sufficient for both viral infection and propagation, it was next asked whether oligodendrocytes were even necessary for viral spread in vivo. To this end, Mad-1 JCV was injected into the callosa of 16 week-old rag1−/− immunodeficient but myelin wild-type human glial chimeric mice. These normally-myelinated mice recruit few if any oligodendrocytes from the engrafted progenitor pool, so that their human cell complement remains limited to glial progenitors and astrocytes (Han et al., "Forebrain Engraftment by Human Glial Progenitor Cells Enhances Synaptic Plasticity and Learning in Adult Mice," *Cell Stem Cell* 12:342-353 (2013), which is hereby incorporated by reference in its entirety). Twelve weeks after viral injection, at 28 weeks of age, the expansion of VP1+ infected cells within these myelin wild-type human astroglial chimeric hosts was grossly similar to that of human glial chimeric myelin-deficient shiverer mice, in which infected donor-derived human oligodendroglia are admixed with infected GPCs and astrocytes (FIG. 5A compare to FIG. 4A). Importantly though, the compartmental pattern of viral spread differed in the recipient phenotypes. In the myelin wild-type glial chimeras, in which human donor cells integrated only as astrocytes and GPCs but not oligodendrocytes (FIG. 5C), JCV infection predominated in the cortex and striatum. This contrasted sharply to the pattern of viral spread in the chimeric shiverer mice, in which human cells also engrafted as oligodendrocytes and fibrous astrocytes, and in which JCV infection was noted to preferentially spread in the white matter (FIG. 5E). These observations indicated that oligodendroglia are not necessary for JCV propagation in vivo, and that astroglia are sufficient to support viral infection and spread. As such, these data strongly support the notion that astrocytes and GPCs serve as the principal reservoirs for JCV in vivo.

Example 6

JCV-Infected Olgodendrocytes Enter the Cell Cycle

Figure 6:
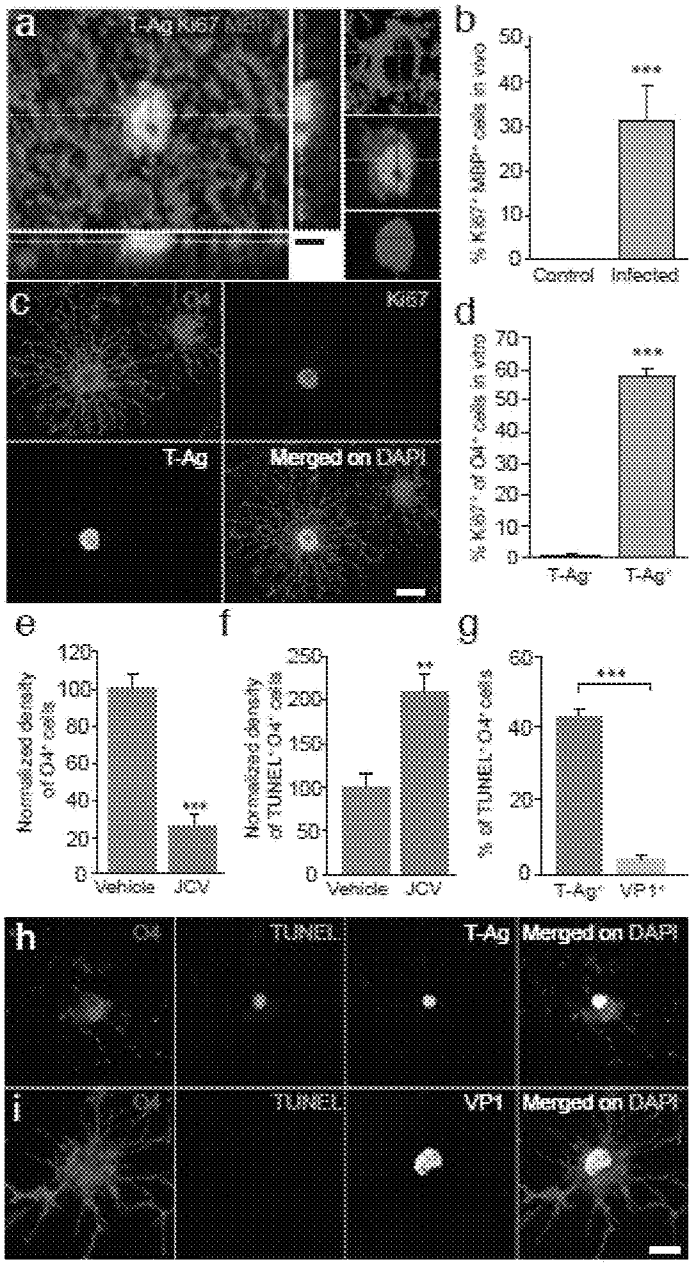
FIGS. 6A-I show JCV-infection leads to cell cycle entry associated with oligodendrocytic death.

Polyoma large T antigen (T-Ag) can trigger cell cycle entry and S-phase initiation by a variety of mitotically-quiescent somatic cell types, via binding to retinoblastoma protein (pRb). The resultant progression to S-phase both permits and accelerates viral replication (Dickmanns et al., "The Kinetics of Simian Virus 40-Induced Progression of Quiescent Cells into S Phase Depend on Four Independent Functions of Large T Antigen," *J. Virol.* 68:5496-5508 (1994), which is hereby incorporated by reference in its entirety). On that basis, it was next asked whether cell cycle initiation occurs in JCV-infected oligodendrocytes in PML, and if so whether the induction of cell cycle in post-mitotic human oligodendroglia was sufficient to trigger their death. To that end, infected oligodendrocytes in the engrafted shiverer/rag2-null mouse were immunolabeled for the mitosis-associated antigen Ki67, and it was found that 31.0 f 8.4% of infected mature MBP+ oligodendrocytes were indeed Ki67+(FIG. 6A). In contrast, no MBP+, Ki67+ oligodendrocytes were found in matched uninfected controls (FIG. 6B).

To further investigate the relationship of JCV infection to aberrant oligodendrocytic cell cycle entry, cultured oligodendrocytes derived from CD140a+ human fetal GPCs were then infected. The plated GPCs were differentiated in vitro into 04+ oligodendroglia over 7 days, then infected with MAD-1 JCV at $10^5$ genome equivalents/cell. When assessed 5 days post-infection (DPI), 26.5±2.2% of oligodendrocytes expressed LgT antigen (FIG. 6C), while only 1.3±0.6% expressed VP-1. When reassessed at 10 DPI, 58.4±2.0% of the T-Ag+JCV-infected oligodendrocytes co-expressed Ki67, indicating their aberrant entry into cell cycle. Uninfected, T-Ag-oligodendrocytes in the same cultures exhibited no appreciable Ki67 expression (FIG. 6D). These findings support the in vivo observation of Ki67+MBP+ oligodendroglia in JCV-injected human glial chimeric shiverer mice (FIGS. 6A-B), and suggest that otherwise post-mitotic human oligodendroglia may be aberrantly induced into cell cycle entry by JCV infection.

Example 7

JCV-Induced Cell Cycle Entry is Associated with Oligodendrocytic Death

It was next asked whether the large T antigen-associated induction of oligodendrocytic cell cycle entry was sufficient to trigger oligodendrocytic death, since ectopic cell cycle entry has been associated with cell death in a variety of otherwise post-mitotic phenotypes. In particular, an analogous process of cell cycle activation-induced death has been described extensively in neurons, in which it has been explored as a mechanism of neurodegenerative cell loss (Busser et al., "Ectopic Cell Cycle Proteins Predict the Sites of Neuronal Cell Death in Alzheimer's Disease Brain," *J. Neurosci.* 18:2801-2807 (1998); Herrup et al., "Divide and Die: Cell Cycle Events as Triggers of Nerve Cell Death," *J. Neurosci.* 24:9232-9239 (2004); Yang et al., "Neuronal Cell Death is Preceded by Cell Cycle Events At All Stages of Alzheimer's Disease," *J. Neurosci.* 23:2557-2563 (2003), which are hereby incorporated by reference in their entirety).

In vitro, it was found that the number of viable oligodendrocytes was significantly decreased 10 days following infection (10 DPI) with type 2A Mad-1 JCV, relative to otherwise matched uninfected controls (FIG. 6E). The diminished oligodendrocytic numbers of infected cultures were accompanied by a significant increase in the number of infection-associated dying oligodendrocytes, as defined by terminal deoxynucleotidyl transferase dUTP nick end-labeling (TUNEL) (Negoescu et al., "In situ Apoptotic Cell Labeling by the TUNEL Method: Improvement and Evaluation on Cell Preparations," *J. Histochem. Cytochem.* 44:959-968 (1996), which is hereby incorporated by reference in its entirety) (FIG. 6F). Large T antigen was expressed by 43.5±2.1% of TUNEL+ oligodendrocytes at 10 DPI, while only 4.6±0.3% of TUNEL+ oligodendrocytes expressed VP1+(n=4 each; $p<0.01$) (FIG. 6G). These in vitro data indicate that the vast majority of oligodendrocytes killed by JCV infection die in association with LgT expression, never progressing to the point of VP1-defined viral replication. Furthermore, in JCV8 infected human glial chimeras, sporadic apoptotic oligodendroglia were identified by TUNEL labeling in vivo, and it was found that a large proportion of these TUNEL+ oligodendroglia expressed the mitotic marker Ki67, indicating that their deaths in temporal association with aberrant cell cycle entry. Such apoptotic loss was not observed in infected astrocytes, which instead assumed the hypertrophic appearance of infected pre-lytic cells prior to death. Together, these data strongly suggested that oligodendrocytic death ensues in response to JCV is primarily apoptotic, and occurs in response to large T-triggered forced cell cycle entry rather than to replication-associated cytolysis.

Example 8

Cell Cycle Arrest at G2/M Transition in Astrocytes and OPCs

Figure 7:
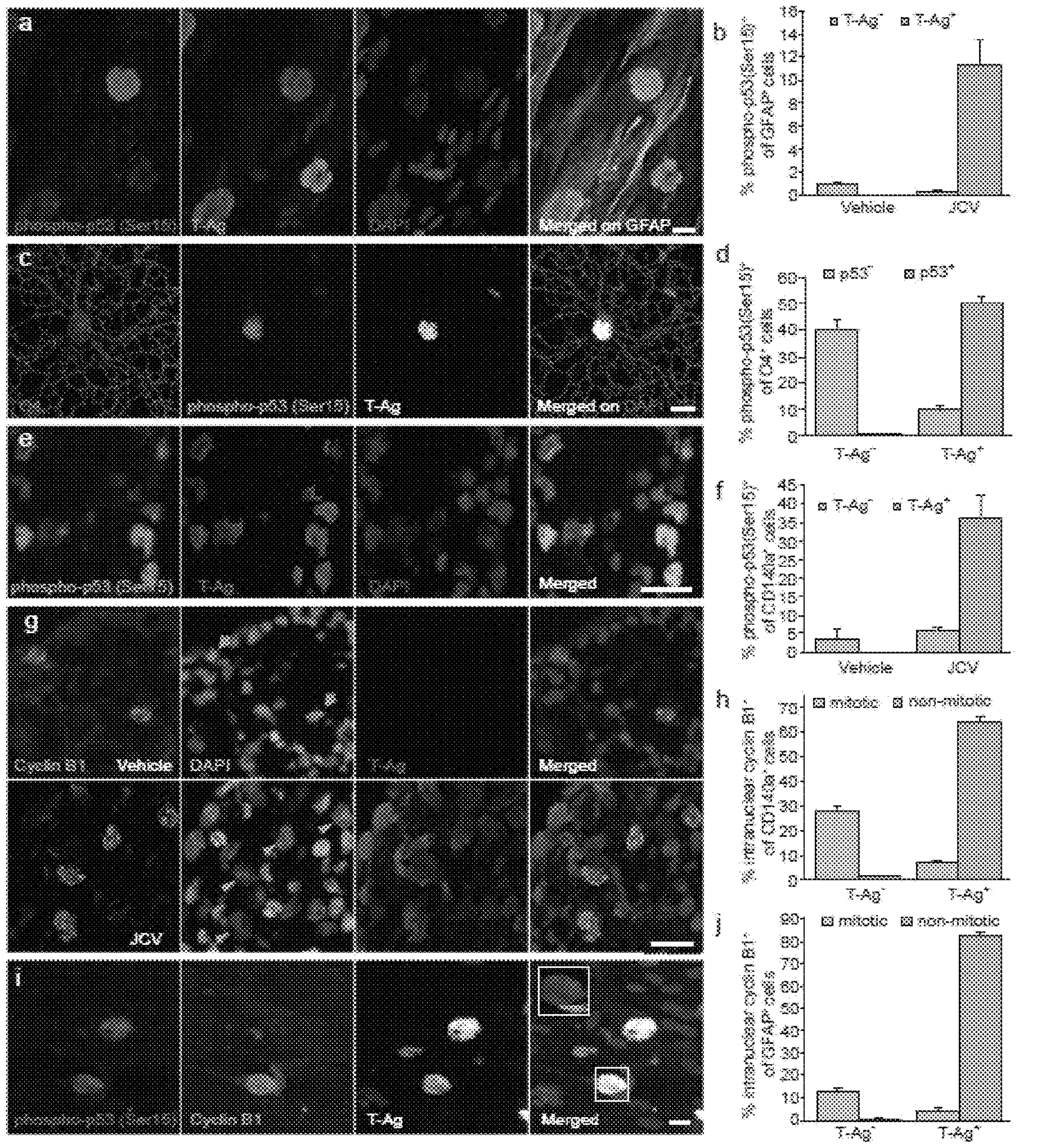
FIGS. 7A-J show cell cycle arrest at G2/M transition in astrocytes, oligodendrocytes and OPCs. Large T antigen+ glia expressed nuclear cyclin B1, as well as phospho-p53 (Ser15), regardless of their mitotic stage.

Polyoma viral replication requires S-phase progression on the part of infected host cells. In particular, previous studies had revealed that JCV genome replication may be facilitated by virally induced cell cycle arrest in G2, prior to the G2/M transition (Orba et al., "Large T Antigen Promotes JC Virus Replication in G2-Arrested Cells by Inducing ATM- and ATR-mediated G2 Checkpoint Signaling," *J Biol Chem* 285:1544-1554 (2010), which is hereby incorporated by reference in its entirety). In light of the apparent delay in viral replication in human oligodendroglia, relative to astrocytes and glial progenitors, it was next asked whether infected astrocytes and oligodendrocytes might differ in their efficiency of S/G2 traversal. Since data indicates that astrocytes and GPCs are the principal vectors of viral spread in vivo, the cell cycle status of JCV-infected astroglia was first investigated, by focusing on cyclin B1, which is normally expressed in the cytoplasm in G2 and enters the nucleus only at the initiation of M phase. It was found that LgT+ glia expressed nuclear cyclin B1, as well as phospho-p53(Ser15), regardless of their mitotic stage (FIG. 7A-B). DAPI staining revealed the frequent presence of JCV infected cells with nuclear cyclin B1+ that were not mitotic (FIG. 7C-D), suggesting that JCV infection was associated with cell cycle arrest.

To further define the possibility of phenotype-selective cell cycle arrest by JCV, the state of p53 phosphorylation in JCV-infected human oligodendrocytes and astrocytes was investigated. p53 is phosphorylated at Ser15 when DNA damage is detected, so that phospho-p53(Ser15) expression may be used as a marker of DNA damage, as well as its associated cell cycle arrest at G2/M (Orba et al., "Large T Antigen Promotes JC Virus Replication in G2-Arrested Cells by Inducing ATM- and ATR-Mediated G2 Checkpoint Signaling," *J. Biol. Chem.* 285:1544-1554 (2010); Banin et al., "Enhanced Phosphorylation of p53 by ATM in Response to DNA Damage," *Science* 281:1674-1677 (1998); Shieh et al., "DNA Damage-Induced Phosphorylation of p53 Alleviates Inhibition by MDM2*,*" *Cell* 91:325-334 (1997), which are hereby incorporated by reference in their entirety). It was found that 83.6±0.9% (n=4) of LgT+ oligodendrocytes co-expressed phosphop53(Ser15), while only 1.3±0.8% of uninfected cells did so (FIG. 7E-F), strongly suggesting that JCV infection was associated with G2/M checkpoint arrest. To further assess this possibility in astrocytes, cell cycle analysis of JCV-infected human astroglia, derived from GPCs exposed to high serum for 10 days, then exposed to JCV and analyzed 14 days later was conducted. It was noted that the JCV infected LgT+ astrocytes indeed exhibited a marked accumulation of cells in G2/M relative to their uninfected controls (FIG. 8A). Interestingly, a fraction of these infected astrocytes appeared hyperploid, suggesting ongoing DNA replication in infected astroglia, despite their relative cell cycle arrest (FIG. 8B).

Similarly, among CD140a-immunoselected glial progenitor cells infected with type 2A (MAD-1) JCV, 60.8±3.6% (n=4) expressed T-Ag+ and 36.1±6.1% expressed phospho-p53(Ser15), while only 3.2% of uninfected GPCs expressed phospho-p53(Ser15)+(FIG. 7G-H). Cyclin B1 immunoreactivity was localized to the hypertrophic nuclei of infected GPCs, just as in astrocytes (FIG. 7G and FIG. 7I), and large T antigen+ infectants of both phenotypes were noted to co-express cyclin B1 and phospho-p53 (Ser15) even when not mitotic (FIG. 7J). Together, these results suggest that JCV infection of human glia triggers phosphorylation of p53 at Ser15 with concomitant cell cycle arrest at G2/M. Whereas this event appears to trigger apoptotic cell death in oligodendrocytes, it seems associated with lytic replication of the viral genome in astrocytes and glial progenitor cells.

Example 9

JCV VP-1 Rapidly Mutated In Vivo

In PML, point mutations in the VP1 capsid gene have been reported at multiple sites of the sialic acid binding region, yet neither the genesis nor pathogenic role of these mutations has been clear (Gorelik et al., "Progressive Multifocal Leukoencephalopathy (PML) Development is Associated With Mutations in JC Virus Capsid Protein VP1 That Change its Receptor Specificity," *J. Infect. Dis.* 204:103-114 (2011); Reid et al., "Sequencing and Analysis of JC Virus DNA From Natalizumab-Treated PML Patients," *J. Infect. Dis.* 204:237-244 (2011), which are hereby incorporated by reference in their entirety). Since the propagation and spread of JCV in the human glial chimeric brains was so robust, it was next asked whether JCV mutation might be identified during its replication and spread in this system. To assess viral evolution during active infection in vivo, 3 sections from each of 4 JCV-infected brains from mice killed 8-11 weeks after viral infection were sampled. All mice had been neonatally implanted with human GPCs, and were given intracallosal injections of MAD1 JCV between 4-8 weeks of age. Three of the 4 mice were homozygous shiverers, in which donor human GPCs, astrocytes and oligodendrocytes co-existed, and 1 was a wild-type for myelin, which are chimeric only for human donor-derived astrocytes and GPCs. TA PCR cloning was used to clone and sequence JCV VP1 DNA from a total of 32 viral clones per sampled section, or 96 per mouse. The VP1 segment of each clone was sequenced and aligned with wild-type MAD1 JCV, whose sequence was validated and confirmed in matched aliquots of the injected virus. Among the 480 clones sequenced from the 5 JCV-injected mice, 155 (32%) VP-1 genomic mutations were noted compared to the wild-type MAD1 sequence. 125 of these yielded mutations in protein sequence. Of these muteins, only 15 distinct loci were represented twice or more in the overall set (Table 1).

TABLE 1

| Length of infection (wks) | Age at infection (wks) | Host genotype | Non-synonymous mutations occurring more than once (number of occurrences) | Total number of non-synonymous mutant VP1 sequences |
|---|---|---|---|---|
| 3.5 | 16.1 | shi/rag2—/— | — | 17 |
| 8 | 11.6 | shi/rag2—/— | G8del (2)<br>S72Y (9)<br>S61L (5)<br>R266T/G (6) | 42 |

TABLE 1-continued

| Length of infection (wks) | Age at infection (wks) | Host genotype | Non-synonymous mutations occurring more than once (number of occurrences) | Total number of non-synonymous mutant VP1 sequences |
|---|---|---|---|---|
| 11.6 | 8.1 | shi/rag2—/— | V233I (3) | 18 |
| | | | S123C (3) | |
| 11.6 | 8.1 | shi/rag2—/— | G57S (2) | 18 |
| | | | D66G (2) | |
| | | | Y38A (2) | |
| | | | V156A (2) | |
| | | | L354P (2) | |
| | | | E328G (2) | |
| 12 | 16.4 | ragl— | K60Q (2) | 30 |
| | | | F68L (7) | |
| | | | S123C (7) | |
| | | | G125V (3) | |
| Starting virus | | | H122Y/P(3) | 4 |

The VP1 gene is mutated in the glial chimeric mouse brain following infection with JCV Human GPC-engrafted shiverer/rag2-null or normally myelinated ragl-null mice were infected with the Mad-1 variant of JCV for periods of time ranging from 4-12 weeks. TA PCR cloning was used to sequence JCV VP1 DNA from 96 viral clones/mouse, taken at three different anteroposterior levels (anterior forebrain, the site of JCV injection, and posterior forebrain). Among the 384 clones sequenced from the 4 JCV-injected mice, 129 VP-1 mutations were noted relative to the initial sequence of wild-type type 1A (Mad-1) JCV. Of the 129 muteins, 15 were represented two or more times in the overall set. Mutations that occurred more than once in a single animal are listed, with the number of mutations in parentheses. Note that S123C and D66G have been reported in PML (Frisque, R. J., "Regulatory Sequences and Virus-cell Interactions of JC Virus," *Prog Clin Biol Res* 105: 41-59 (1983), which is hereby incorporated by reference in its entirety).

These included 2 mutations—S 123C and D66G—which have been described in JCV isolated from patients with active PML (Gorelik et al., "Progressive Multifocal Leukoencephalopathy (PML) Development is Associated With Mutations in JC Virus Capsid Protein VP1 That Change its Receptor Specificity," *J. Infect. Dis.* 204:103-114 (2011); Reid et al., "Sequencing and Analysis of JC Virus DNA From Natalizumab-Treated PML Patients," *J. Infect. Dis.* 204:237-244 (2011), which are hereby incorporated by reference in their entirety). Each of these lies within the sialic acid binding site of VP1, of particular note since VP1 mutants may lose sialic acid dependence for their binding to host cells; this suggests the possibility that specific JCV VP1 mutants may acquire selective advantage during host infection (Gorelik et al., "Progressive Multifocal Leukoencephalopathy (PML) Development is Associated with Mutations in JC Virus Capsid Protein VP1 That Change its Receptor Specificity," *J.* Infect. Dis. 204:103-114 (2011), which is hereby incorporated by reference in its entirety). This in turn suggests that capsid protein mutations occurring during viral propagation may dynamically shift the infectivity and phenotypic specificity of JCV in vivo, during the course of a single host's infection.

Example 10

VP1 Mutants were Infective but Showed No Phenotypic Preferences

Figure 9:
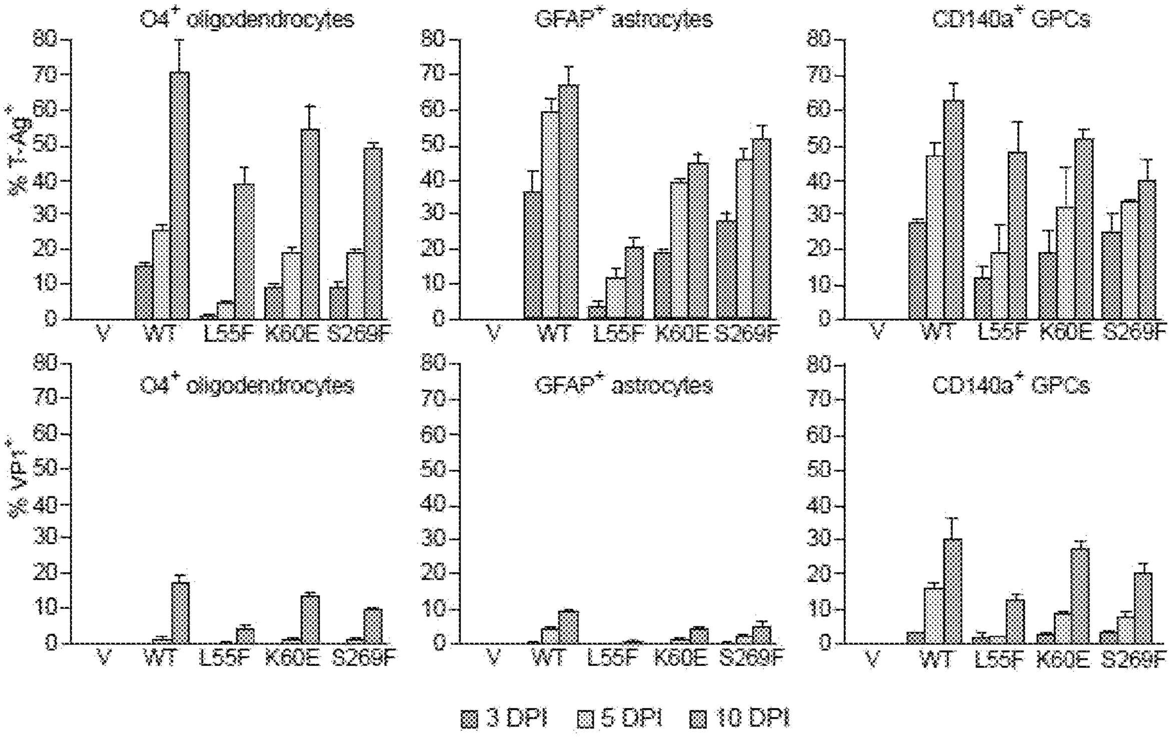
FIG. 9 shows infectivity of type 2A (Mad-1 NCCR) JCV VP1 mutants in oligodendrocytes, astrocytes, and GPCs in vitro. The VP1 mutants infected each tested cell type less efficiently than did wild-type JCV; the L55F mutein was the least effective. Nonetheless, by 10 DPI, all cell types were robustly infected by each tested VP1 mutein. JCV propagated more effectively in OPCs than in astrocytes. For example, 3.5% of type 2A WT JCV-infected OPCs expressed VP1 as early as 3 DPI, whereas only 0.2% of astrocytes were VP1+ at that early time-point. Data are mean±SEM (n=4/group, triplicate wells).

On the basis of these observations, it was next asked if JCV mutants carrying PML-associated VP1 mutations could infect human glia as well as parental JCV, and if so, whether their relative infectivities differed in either virulence or phenotypic specificity. To that end, the infectivities of 3 VP1 mutations of type 2A JCV (all with PML-associated Mad-1 NCCR) was assessed both in vitro and in vivo. These VP-1 capsid mutants included L55F, K60E, and S269F, each isolated from a different PML patient. Each mutant was first assessed in vitro, and it was found that each robustly infected human oligodendrocytes, astrocytes, and GPCs (FIG. 9). On that basis, the in vivo infectivities of the two most frequent PML associated mutations, L55F and S269F, were assessed. Either WT VP1 or mutant VP1 type 2A JCV were injected into the corpus callosum of human glial chimeras at 14 weeks of age, and the mice killed 5 weeks later. Histological analysis revealed that each mutant elicited robust infection in the host, with a recapitulation of both glial infection and local demyelination. At the single timepoint assessed, no overt differences were noted in the respective infectivities of glial progenitors, astrocytes or oligodendrocytes by WT VP1 JCV, relative to its two VP1-mutant variants (FIG. 10). All three viruses manifested robust infection in these human glial chimeric mice.

Discussion of Examples 1-10

In this study, human glial chimeric mice were used to establish an in vivo model of JCV viral infection and demyelination, which mimics the salient features of progressive multifocal leukoencephalopathy. It was found that in neonatally-engrafted MBPshi/shi mice chimeric for human oligodendrocytes as well as astrocytes, oligodendrocytic death and demyelination followed astrocytic infection. Astrocytic infection by JCV proved far more efficient and prevalent than oligodendrocytic infection in vitro, while in vivo, JCV appeared to propagate primarily via glial progenitor cells and astroglia, and much less robustly so in central oligodendrocytes. Indeed, astrocytes proved sufficient for viral propagation in vivo, with viral spread occurring rapidly and robustly in mice chimeric only for human GPCs and astrocytes, and utterly lacking human oligodendrocytes.

While human oligodendrocytes exhibited much less frequent viral replication than did astrocytes and progenitors, their infection-associated loss and concomitant demyelination was profound. All macroglial phenotypes were targeted and lost following intracerebral injection of JCV. Yet whereas astrocytic death was associated with cellular lysis in the setting of viral replication and spread, oligodendrocytic death was instead presaged by the aberrant cell cycle entry of these otherwise post-mitotic cells, leading to their arrest in G2 and subsequent death. Thus, the oligodendrocytic loss and demyelination of JCV-infected human glial chimeras appeared to result from LgT-dependent cell cycle induction leading to oligodendrocytic death before viral replication. As such, while VP1-reported viral replication was manifest in oligodendrocytes, its incidence was substantially less than that of astrocytes. As a result, when assessed at 5 weeks post-infection, a large proportion of LgT+ oligodendrocytes co-expressed Ki67, while oligodendrocytic expression of the replication associated VP-1 protein was uncommon. The data therefore suggests a picture of viral propagation and amplification in an astrocytic reservoir, followed by oligodendrocytic infection, apoptotic death and demyelination, but with little oligodendrocytic viral replication.

Importantly, viral spread within infected brains was associated with rapid and progressive mutation, presumably within the astrocytic reservoir of infection. This process of serial and progressive mutation may provide a selective advantage to the most virulent viral mutants within individual brains, and thus result in the acceleration of viral spread and cytopathogenicity with time. One might then anticipate the emergence and selection of dominant JCV mutants with time during disease progression in any given patient. While JCV mutations have been noted to arise during the course of disease, and have been well-documented in VP-1 (Gorelik et al., "Progressive Multifocal Leukoencephalopathy (PML) Development is Associated With Mutations in JC Virus Capsid Protein VP1 That Change its Receptor Specificity," *J. Infect. Dis.* 204:103-114 (2011); Reid et al., "Sequencing and Analysis of JC Virus DNA From Natalizumab-Treated PML Patients," *J. Infect. Dis.* 204:237-244 (2011), which are hereby incorporated by reference in their entirety), mutation in JCV's non-coding regulatory regions may be especially critical to disease progression (Frisque, R. J., "Regulatory Sequences and Virus-cell Interactions of JC Virus," *Prog. Clin. Biol. Res.* 105:41-59 (1983); Kim et al., "Glial Cell-specific Regulation of the JC Virus Early Promoter by Large T Antigen," *J. Virol.* 74:755-763 (2000); Pfister et al., "JC Virus Regulatory Region Tandem Repeats in Plasma and Central Nervous System Isolates Correlate with Poor Clinical Outcome in Patients with Progressive Multifocal Leukoencephalopathy," *J. Virol.* 75:5672-5676 (2001), which are hereby incorporated by reference in their entirety). Together, these observations suggest that the clonal selection of more infective mutants may occur naturally in human hosts (Sunyaev et al., "Adaptive Mutations in the JC Virus Protein Capsid are Associated with Progressive Multifocal Leukoencephalopathy (PML)," *PLoS Genet.* 5:e1000368 (2009), which is hereby incorporated by reference in its entirety). If so, such clonal evolution might account for the terminal acceleration of demyelination often observed in PML patients.

Large T antigen can induce aberrant cell cycle entry and S-phase initiation in a variety of somatic phenotypes, through its binding to the tumor suppressor retinoblastoma protein (Rb) and consequent de-repression of Rb targets (Dickmanns et al., "The Kinetics of Simian Virus 40-Induced Progression of Quiescent Cells into S Phase Depend on Four Independent Functions of Large T Antigen," *J. Virol.* 68:5496-5508 (1994); Caracciolo et al., "Role of the Interaction Between Large T Antigen and Rb Family Members in the Oncogenicity of JC Virus," *Oncogene* 25:5294-5301 (2006); DeCaprio et al., "SV40 Large Tumor Antigen Forms a Specific Complex with the Product of the Retinoblastoma Susceptibility Gene," *Cell* 54:275-283 (1988); Saenz-Robles et al., "Intestinal Hyperplasia Induced by Simian Virus 40 Large Tumor Antigen Requires E2F2," *J. Virol.* 81:13191-13199 (2007); Xiao et al., "Astrocyte Inactivation of the pRb Pathway Predisposes Mice to Malignant Astrocytoma Development that is Accelerated by PTEN Mutation," *Cancer Cell* 1:157-168 (2002), which are hereby incorporated by reference in their entirety). Whereas some mitotic phenotypes may undergo neoplastic transformation by this process—and the polyomaviruses have been causally-linked to oncogenesis in a variety of species and cell types (Hermeking et al., "Role of C-myc in Simian Virus 40 Large Tumor Antigen-Induced DNA Synthesis in Quiescent 3T3-L1 Mouse Fibroblasts," *Proc. Nat'l. Acad. Sci. USA* 91:10412-10416 (1994); Krynska et al., "Role of Cell Cycle Regulators in Tumor Formation in Transgenic Mice Expressing the Human Neurotropic Virus, JCV, Early Protein," *J. Cell Biochem.* 67:223-230 (1997); London et al., "Brain Tumors in Owl Monkeys Inoculated with a Human Polyomavirus (JC Virus)," *Science* 201:1246-1249 (1978); Manfredi et al., "The Transforming Activity of Simian Virus 40 Large Tumor Antigen," *Biochimica et Biophysica Acta* 1198:65-83 (1994); Tevethia et al., "A Simian Virus 40 Large T-antigen Segment Containing Amino Acids 1 to 127 and Expressed Under the Control of the Rat Elastase-1 Promoter Produces Pancreatic Acinar Carcinomas in Transgenic Mice," *J. Virol.* 71:8157-8166 (1997); Walker et al., "Human Papovavirus (JC): Induction of Brain Tumors in Hamsters," *Science* 181:674-676 (1973), which are hereby incorporated by reference in their entirety)—in post-mitotic phenotypes as human oligodendrocytes, Rb de-repression may instead trigger p53-dependent apoptotic cell death (Herrup et al., "Divide and Die: Cell Cycle Events as Triggers of Nerve Cell Death," *J. Neurosci.* 24:9232-9239 (2004), which is hereby incorporated by reference in its entirety). The data thus suggests JCV infection-induced T antigen may initiate apoptotic oligodendrocytic death via aberrant cell cycle induction, followed by p53-dependent apoptotic cell death before viral replication can be completed. While both the in vitro and in vivo data suggest that this is the dominant mechanism of JCV-induced oligodendrocytic death, a minority of infected oligodendroglia did progress to viral replication and VP-1 expression, suggesting that at least some oligodendroglia may activate mechanisms for apoptotic escape, such as the expression of inhibitors of apoptosis such as survivin, a mechanism that may dominate in astroglia (Pina-Oviedo et al., "Effects of JC Virus Infection on Anti-apoptotic Protein Survivin in Progressive Multifocal Leukoencephalopathy," *Am. J. Pathol.* 170:1291-1304 (2007), which is hereby incorporated by reference in its entirety). Why some JCV-infected oligodendroglia progress to viral replication, while most instead die before reaching that stage, remains unclear, although this might be a function of the developmental stage at which individual oligodendroglia—or their progenitors—are infected. Besides these avenues of death by infected oligodendroglia, the frequent identification of dying oligodendrocytes lacking any antigenic evidence of viral infection suggests the co-incidence of additional mechanisms for oligodendrocytic loss in JCV-infected brains. Recent studies have highlighted the dependence of oligodendrocytes on local astrocytes (Bruck et al., "Reduced Astrocytic NF-kappaB Activation by Laquinimod Protects From Cuprizone-Induced Demyelination," *Acta Neuropathol* 124:411-424 (2012), which is hereby incorporated by reference in its entirety), and that of neurons upon oligodendroglia (Funfschilling et al., "Glycolytic Oligodendrocytes Maintain Myelin and Long-term Axonal Integrity," *Nature* 485:517-521 (2012); Benediktsson et al., "Neuronal Activity Regulates Glutamate Transporter Dynamics in Developing Astrocytes," *Glia* 60:175-188 (2012), which are hereby incorporated by reference in their entirety). As such, given the marked astroglial pathology so evident in JCV-infected brains, the withdrawal of metabolic support of oligodendrocytes by infected astroglia, as well as the latter's potential paracrine cytotoxicity (Bruck et al., "Reduced Astrocytic NF-kappaB Activation by Laquinimod Protects From Cuprizone-induced Demyelination," *Acta Neuropathol.* 124:411-424 (2012), which is hereby incorporated by reference in its entirety), might contribute substantially to both oligodendrocytic loss and its associated neuropathology. Oligodendrocytic loss and demyelination in PML may then comprise secondary events, reflecting a combination of paracrine toxicity by infected astroglia, a loss of astroglial support of local oligodendrocytes, and apoptotic oligodendrocytic death following direct infection. Complicating matters further, each of these mechanisms may be dynamically modulated by concurrent JCV mutation, occurring within a contiguous astrocytic reservoir of virus.

Besides identifying astrocytes and their progenitors as principal substrates for JCV propagation in vivo, with oligodendrocytic death a secondary consequence of viral propagation, this astroglial-centric view of PML pathogenesis may have significant clinical implications, both for disease presentation and treatment. Patients with PML frequently manifest encephalopathic confusion and cognitive deficits long before frank radiographic evidence of demyelination is noted. These results suggest the possibility that the clinical deterioration in these patients may reflect progressive astrocytic dysfunction, especially given the strong influence that astrocytes have on synaptic coordination and plasticity (Han et al., "Forebrain Engraftment by Human Glial Progenitor Cells Enhances Synaptic Plasticity and Learning in Adult Mice," *Cell Stem Cell* 12:342-353 (2013); Kang et al., "Astrocyte-Mediated Potentiation of Inhibitory Synaptic Transmission," *Nature Neurosci.* 1:683-692 (1998); Araque et al., "Tripartite Synapses: Glia, the Unacknowledged Partner," *Trends Neurosci.* 22:208-215 (1999); Paukert et al., "Reduction of Motion Artifacts During In Vivo Two-Photon Imaging of Brain Through Heartbeat Triggered Scanning," *J. Physiol.* 590:2955-2963 (2012), which are hereby incorporated by reference in their entirety). Even a profound degree of astrocytic pathology may not have been previously noted in PML patients, since magnetic resonance imaging of the brain is highly biased towards identifying signal normalities in the white matter. Contemporary MRI has been relatively insensitive to gray matter disruption. Similarly, little focused investigation of astrocytes has been performed in studies of human pathological samples, which have emphasized oligodendrocytic loss and demyelination (Gerber et al., "Immunohistochemical Demonstration of Common Antigen of Polyomaviruses in Routine Histologic Tissue Sections of Animals and Man," *Am. J. Clin. Pathol.* 73:795-797 (1980); Greenlee et al., "Immunoenzymatic Labelling of JC Papovavirus T Antigen in Brains of Patients with Progressive Multifocal Leukoencephalopathy," *Acta Neuropathol.* 71:150-153 (1986); Jochum et al., "Detection of JC Virus by Anti-VP1 Immunohistochemistry in Brains with Progressive Multifocal Leukoencephalopathy," *Acta Neuropathol.* 94:226-231 (1997); Mazlo et al., "Morphological Demonstration of the First Phase of Polyomavirus Replication in Oligodendroglia Cells of Human Brain in Progressive Multifocal Leukoencephalopathy (PML)," *Acta Neuropathol.* 49:133-143 (1980); Richardson-Burns et al., "Progressive Multifocal Leukoencephalopathy and Apoptosis of Infected Oligodendrocytes in the Central Nervous System of Patients With and Without AIDS," *Arch. Neurol.* 59:1930-1936 (2002); Zurhein et al., "Particles Resembling Papova Viruses in Human Cerebral Demyelinating Disease," *Science* 148:1477-1479 (1965), which are hereby incorporated by reference in their entirety), although the early infection of astrocytes in PML has been noted (Ironside et al., "The Identification of Cells Containing JC Papovavirus DNA in Progressive Multifocal Leukoencephalopathy by Combined In Situ Hybridization and Immunocytochemistry," *J. Pathol.* 157:291-297 (1989); Astrom et al., "Early Pathological Changes in Progressive Multifocal Leukoencephalopathy: A Report of Two Asymptomatic Cases Occurring Prior to the AIDS Epidemic," *Acta Neuropathol.* 88:93-105 (1994), which are hereby incorporated by reference in their entirety). Together, the results suggest that astrocytes may be both necessary and sufficient for JCV infection of the brain, and that disease-associated astrocytic dysfunction and loss may be at least as important to the neurological deterioration of JCV-infected patients as their progressive demyelination. More broadly, this study also introduces the human glial chimeric mouse brain as a unique preparation by which the natural history of pathogens specific to the human brain may be assessed in vivo, both longitudinally and in real-time, thereby providing fundamentally new opportunities for their mechanistic dissection and therapeutic targeting.

Although preferred embodiments have been depicted and described in detail herein, it will be apparent to those skilled in the relevant art that various modifications, additions, substitutions, and the like can be made without departing from the spirit of the invention and these are therefore considered to be within the scope of the invention as defined in the claims which follow.

What is claimed:

1. A method for infecting in vivo a human astrocyte with JC virus, said method comprising;

providing a non-human mammal comprising with at least 30% of its glial cells in its corpus callosum being human glial cells and/or with at least 5% of its glial cells in its brain white matter being human glial cells and administering intracallosally JC virus into the white matter in the non-human mammal, wherein the JC virus infects and propagates within the human astrocytes and parenchymal progenitor cells of the white mater in the non-human mammal with an efficiency greater than in human oligodendrocytes in the non-human mammal.

2. The method of claim 1 further comprising:

administering a candidate therapeutic agent to the non-human mammal prior to, concurrent with, or after said infecting.

3. The method according to claim 1, wherein at least 15% of all of the glial cells in the white matter of the mammal's brain and/or brain stem are human glial cells.

4. The method according to claim 3, wherein the white matter is cerebellar white matter and at least 50% of all glial cells in the cerebellar white matter are human glial cells.

5. The method according to claim 1, wherein at least 50% of all of the glial cells in the corpus callosum of the mammal are human glial cells.

6. The method according to claim 5, wherein at least 70% of all of the glial cells in the corpus callosum of the mammal are human glial cells.

7. The method of claim 2 further comprising:

determining, as a result of said administering, a therapeutic modification of the human astrocytes in response to the pathogenic infection using a metric selected from the group consisting of morphology, immunophenotype, transcriptionally-regulated reporters, gene expression profiles, mitotic rate, mitotic fraction, metabolic rate, mitochondrial function, oxidative state, telomerase activity, apoptotic index, and net cell survival.

8. The method of claim 1 further comprising:

determining the behavior or fate of the human astrocytes using a metric selected from the group consisting of morphology, immunophenotype, transcriptionally-regulated reporters, gene expression profiles, mitotic rate, mitotic fraction, metabolic rate, mitochondrial function, oxidative state, telomerase activity, apoptotic index, and net cell survival.

9. The method according to claim 8, wherein morphology is examined as reflected in cell size, fiber outgrowth, length, complexity, and indices of myelination efficiency.

10. The method according to claim 9, wherein morphology is examined as reflected in G-ratio, axonal ensheathment efficiency, proportion of axons myelinated, number of axons myelinated per oligodendrocyte, or number of myelin wraps per axon.

11. The method according to claim 8, wherein immunophenotype is examined using immunocytochemistry, immunoblotting, flow cytometry, or fluorescence-activated cell sorting.

12. The method according to claim 8, wherein transcriptionally-regulated reporters are examined using promoter/enhancer-driven reporters in enzymatic or fluorescent form.

13. The method according to claim 8, wherein gene expression profiles are examined using microarrays, real-time PCR, or protein expression profiling.

* * * * *

```
                         SEQUENCE LISTING

<160> NUMBER OF SEQ ID NOS: 2

<210> SEQ ID NO 1
<211> LENGTH: 20
<212> TYPE: DNA
<213> ORGANISM: Artificial Sequence
<220> FEATURE:
<223> OTHER INFORMATION: Primer

<400> SEQUENCE: 1

cctcaatgga tgttgccttt                                              20


<210> SEQ ID NO 2
<211> LENGTH: 17
<212> TYPE: DNA
<213> ORGANISM: Artificial Sequence
```

-continued

```
<220> FEATURE:
<223> OTHER INFORMATION: Primer

<400> SEQUENCE: 2

aaaaccaaag acccctc                                                    17
```